United States Patent [19]

Ohkuma et al.

[11] Patent Number: 4,992,351
[45] Date of Patent: Feb. 12, 1991

[54] RECORDING MEDIUM HAVING A SPECIFIED PHOTOPOLYMERIZATION INITIATOR

[75] Inventors: Norio Ohkuma, Machida; Masanori Takenouchi, Atsugi; Masashi Miyagawa; Tadashi Yamamoto, both of Kawasaki, all of Japan

[73] Assignee: Canon Kabushiki Kaisha, Tokyo, Japan

[21] Appl. No.: 453,171

[22] Filed: Dec. 26, 1989

Related U.S. Application Data

[63] Continuation of Ser. No. 131,068, Dec. 8, 1987, abandoned.

[30] Foreign Application Priority Data

Dec. 9, 1986 [JP] Japan .................. 61-293157
Nov. 6, 1987 [JP] Japan .................. 61-280568

[51] Int. Cl.$^5$ ............... G03C 1/68; B41M 5/26; B41M 5/12; G037 1/727
[52] U.S. Cl. ............... 430/138; 430/281; 430/913; 427/146; 427/150; 428/402.2; 428/402.24; 503/214; 503/215
[58] Field of Search ............... 430/138, 281, 913; 427/150, 146; 503/214, 215; 428/402.2, 402.21, 402.22, 402.24

[56] References Cited

U.S. PATENT DOCUMENTS

| | | | |
|---|---|---|---|
| 3,912,505 | 10/1975 | Goffe et al. | 430/138 |
| 4,366,228 | 12/1982 | Specht et al. | 430/281 |
| 4,440,846 | 4/1984 | Sanders et al. | 430/138 |
| 4,542,084 | 9/1985 | Watanabe et al. | 430/46 |
| 4,576,891 | 3/1986 | Adair et al. | 430/138 |
| 4,632,899 | 12/1986 | Takeda | 430/292 |
| 4,675,269 | 6/1987 | Saccocio et al. | 430/138 |
| 4,701,397 | 10/1987 | Rourke et al. | 430/138 |
| 4,713,312 | 12/1987 | Adair et al. | 430/138 |

FOREIGN PATENT DOCUMENTS

205083 12/1986 European Pat. Off. ............ 400/120

Primary Examiner—Paul R. Michl
Assistant Examiner—Patrick A. Doody
Attorney, Agent, or Firm—Fitzpatrick, Cella, Harper & Scinto

[57] ABSTRACT

A recording medium has a recording layer comprising image-forming elements (A), (B) and (C) containing at least a compound having unsaturated double bond and a photopolymerization initiator. The photopolymerization initiator in the element (A) is a compound represented by the following formula (I):

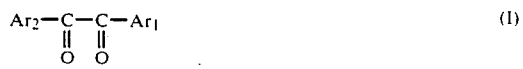

(wherein $Ar_1$ and $Ar_2$ are each aromatic ring or heterocyclis ring). The photopolymerization initiator in the element (B) has an absorption maximum in a wavelength region of 360 to 430 nm. The photopolymerization initiator in the element (C) has an absorption maximum in a wavelength region of 430 nm or longer. The recording medium is suitably used as a transfer recording medium in a recording apparatus which includes heating means and light irradiating means to provide the recording layer with heat energy and photoenergy to change the transfer characteristic of the recording layer. The light irradiating means includes a phosphor of thallium-activated calcium phosphate or thallium-activated calcium zinc phosphate, a phosphor having a fluorescent peak wavelength of 360 to 430 nm and a phosphor having a fluorescent peak wavelength of 430 nm or longer, and a light source for exciting the phosphors.

10 Claims, 15 Drawing Sheets

RECORDING MEDIUM HAVING A SPECIFIED PHOTOPOLYMERIZATION INITIATOR

This application is a continuation of application Ser. No. 131,086, filed Dec. 8, 1987, now abandoned.

FIELD OF THE INVENTION AND RELATED ART

The present invention relates to a recording medium to be used for multi-color image recording.

In the prior art, methods for forming multi-color image by utilization of photopolymerization, are disclosed in "The Mead Microencapsulated Imaging System" SPSE 23rd Fall Symposium on Microimaging Technology, Nov. 15, 1983 and U.S. Pat. No. 4,399,209.

More specifically, in these methods, an imaging sheet comprising a substrate and a coating thereon comprising a chromogenic material and a radiation curable composition encapsulated in rupturable capsules, is provided; the coating is subjected to imagewise exposure with actinic radiation to cure the radiation curable composition and form a latent image; and the latent image is superposed onto a developer sheet comprising a developer layer to form a visible image on the developer sheet.

However, overlapping of the photosensitive regions of the above photopolymerization initiators is large and, for example, as described in U.S. Pat. No. 4,576,891, it was not possible to provide three separate photosensitive wavelength regions unless a photopolymerization initiator and a UV-ray absorber are used in combination and a light with wavelengths in an extremely narrow range is irradiated by use of a band-pass filter. Also, since the band-pass filter is poor in transmittance, a light source of high energy is required. The light source of higher energy makes the apparatus larger in scale, and the apparatus becomes further enlarged in scale to obtain multicolor recording, whereby the apparatus cost also becomes greater undesirably in practical application.

SUMMARY OF THE INVENTION

The present invention has been accomplished in order to solve the above problems of the prior art. More specifically, an object of the present invention is to provide a recording medium which involves little overlapping of the photosensitive wavelength regions of the photopolymerization initiators and yet can give sharp multi-color images even with a light of relatively low energy such as fluorescence.

Another object of the present invention is to provide a recording apparatus having a light source with adequate wavelength region and being capable of giving a multi-color image with little cross-talk.

According to the present invention, there is provided a recording medium having a recording layer comprising image-forming elements (A), (B) and (C) each containing at least a polymerizable compound having an unsaturated double bond (ethylenic unsaturation) and a photopolymerization initiator, the photopolymerization initiator in the element (A) being a compound represented by the following formula (I):

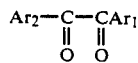  (I)

(wherein $Ar_1$ and $Ar_2$ are each an aromatic ring or a heterocyclic ring), the photopolymerization initiator in the element (B) having an absorption maximum in the wavelength region of 360 to 430 nm and the photopolymerization initiator in said element (C) having an absorption maximum in the wavelength region of 430 nm or longer.

Herein, the term "polymerizable" or "polymerizing" is intended to also cover "crosslinkable" or "crosslinking".

According to the present invention, there is also provided a recording apparatus comprising:

a recording section having a conveying means for conveying a transfer recording medium having a transfer recording layer which changes its transfer characteristic when imparted with heat energy and photoenergy, a heating means for imparting heat energy to the transfer recording medium provided along the conveying route of said transfer recording medium conveyed by said conveying means and a light irradiating means for imparting photoenergy, and a transferring section for transfer of the image formed on the transfer recording medium at the recording section to a transfer-receiving medium, the light irradiating means comprising a phosphor or fluophor composed mainly of either thallium-activated calcium phosphate or thalliumactivated calcium zinc phosphate, a phosphor composed mainly of a compound having a fluorescent peak wavelength in the range of 360 nm or longer and shorter than 430 mn, a phosphor composed mainly of a compound having the fluorescent peak wavelength in the range of 430 nm or longer and 600 nm or shorter, and a light source for exciting the above three kinds of phosphors.

DETAILED DESCRIPTION OF THE INVENTION

Figure 1A:
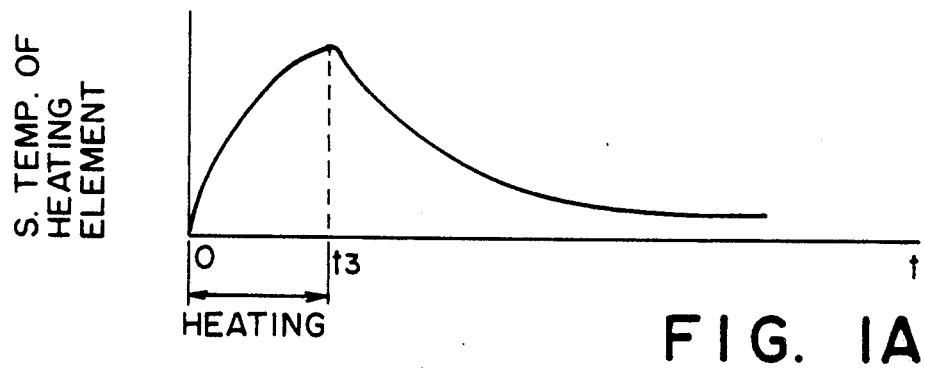
FIG. 1A through 1D illustrate the principle of transfer image formation when forming transfer image with light and heat energies by use of the recording medium of the present invention.

The recording medium of the present invention comprises a support and a transfer recording layer provided on the support. The transfer recording layer is constituted of particulate elements, each containing at least a compound having an unsaturated double bond and a photopolymerization initiator.

The wavelength regions to which the photopolymerization initiators to be used in the present invention are sensitive should be desirably provided by division within the range of about 300 to 600 nm. This is because most of photopolymerization initiators contain an aromatic ring within the molecule and have an absorption band based on the $\pi \rightarrow \pi^*$ transition of the aromatic ring at 300 nm or less, the therefore have sensitivity to the light of 300 nm or shorter, whereby it is difficult to divide the photosensitive wavelength region. On the other hand, with a light having wavelength longer than 600 nm, no sufficient sensitivity can be obtained. The compound represented by the formula (I) gives the maximum sensitivity to the light of about 360 nm or less and therefore is very effective when the photosensitive wavelength region is divided.

In the following, the photopolymerization initiator represented by the following formula (I) contained in the element (A) is described.

In the formula, $Ar_1$ and $Ar_2$ each represent an aromatic ring or heterocyclic ring which may have a substituent, and $Ar_1$ and $Ar_2$ may be the same or different. Also, the photopolymerization initiator of the formula (I) should preferably have the maximum absorption at about 250 nm to about 360 nm. The absorption maximum as herein mentioned refers to the maximum peak when the absorbance of the photopolymerization initiator is measured in chloroform.

Examples of the aromatic ring include benzene ring, naphthalene ring, anthracene ring, indene ring, fluorene ring and others.

Examples of the heterocyclic ring include furan ring, thiophene ring, pyrrole ring, oxazole ring, isooxazole ring, thiazole ring, isothiazole ring, imidazole ring, pyrazole ring, pyrane ring, pyridine ring, pyrrolidine ring, piperidine ring, indole ring, quinoline ring, isoquinoline ring, xanthene ring, carbazole ring, acridine ring, indeline ring, julolidine ring and others.

Among those mentioned above, either one or both of $Ar_1$ and $Ar_2$ should be particularly preferably an aromatic ring, further preferably benzene ring.

The substituent may include hydrogen atom, halogen atom, alkyl, alkoxy, alkylamino, dialkylamino, alkylthio, heterocyclic groups, more specifically, hydrogen atom, methyl, ethyl, isopropyl, tert-butyl, phenyl, trifluoromethyl, cyano, acetyl, ethoxycarbonyl, carboxyl, carboxylate, amino, methylamino, dimethylamino, ethylamino, diethylamino, isopropylamino, diisopropylamino, cyclohexylamino, dicyclohexylamino, acetylamino, piperidino, pyrrolidyl, —PO$_3$H, methoxy, ethoxy, propoxy, isopropoxy, butoxy, pentyloxy, phenoxy, hydroxyl, acetoxy, methylthio, ethilthio, isopropylthio, mercapto, acetylthio, thiocyano, methylsulfinyl, methylsulfonyl, dimethylsulfonyl, sulfonate groups, fluorine atom, chlorine atom, bromine atom, iodyl, trimethylsilyl, triethylsilyl, trimethylstannyl, furyl, thienyl, pyridyl, piperidino, morpholino, pyrrolidyl groups and so on.

Among these substituents, at least one electron donating group such as alkoxy groups such as methoxy, ethoxy, isopropoxy, tert-butoxy or phenoxy groups, methyl, ethyl, isopropyl, hydroxyl, acetoxy, benzoyloxy groups, etc. or a thioalkyl group is preferably contained. Specific examples of the compound of the formula (I) may include the following compounds.

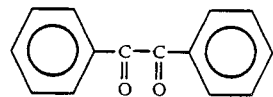

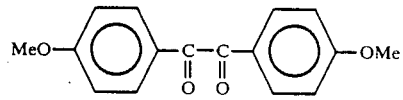

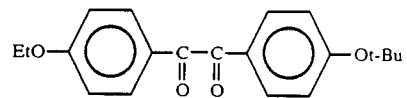

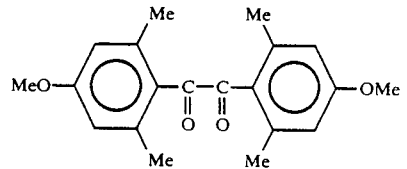

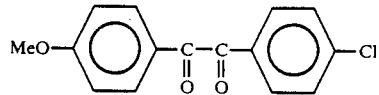

-continued
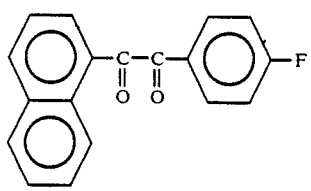
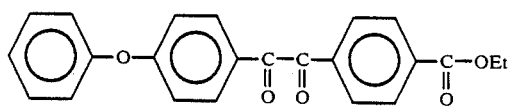
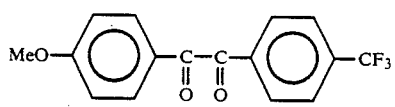
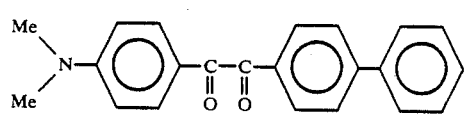
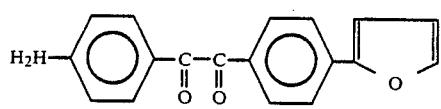
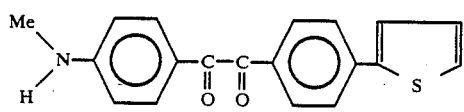
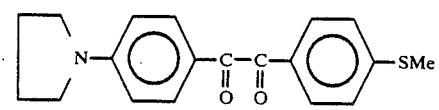
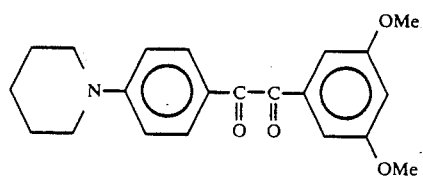
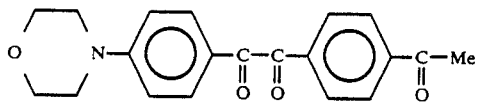
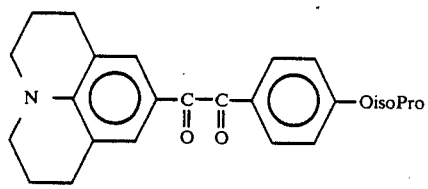

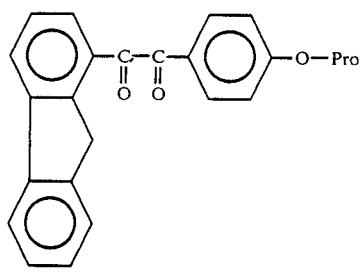
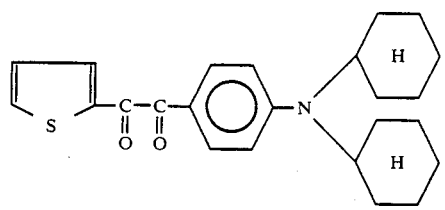
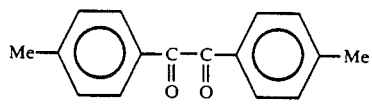
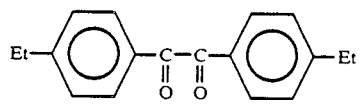
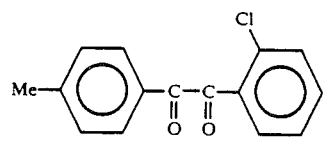
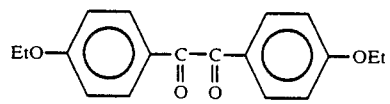
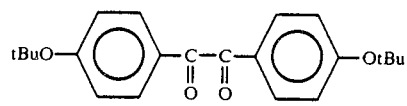
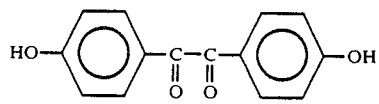
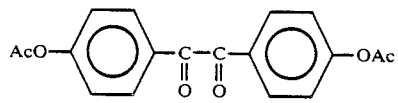
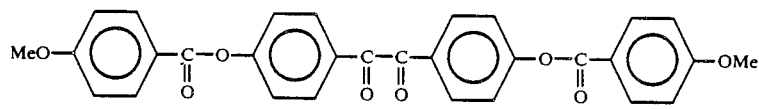
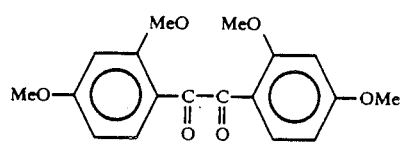

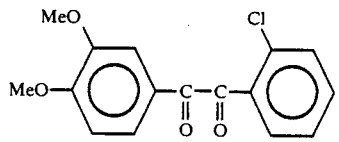
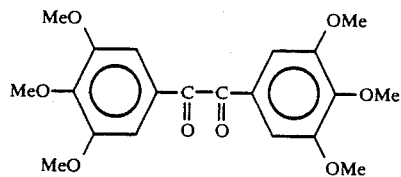
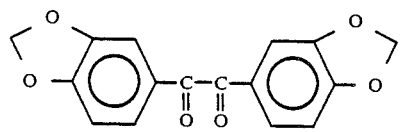
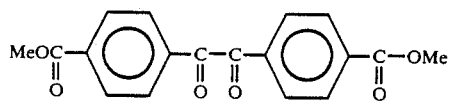
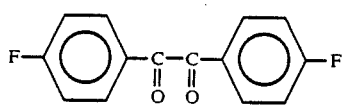
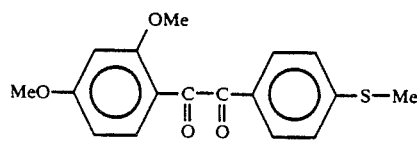
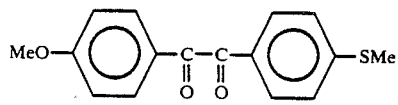
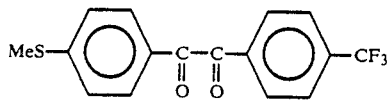
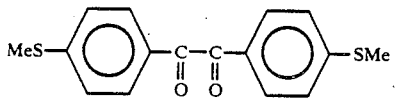
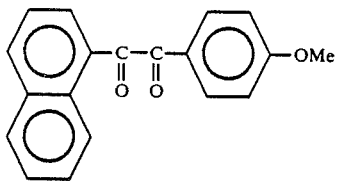
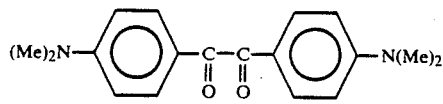
The compound represented by the formula (I) may be synthesized primarily by benzoin condensation.

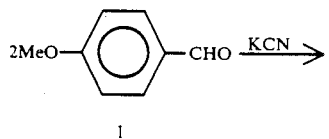

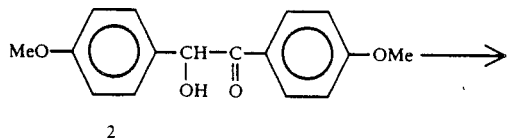

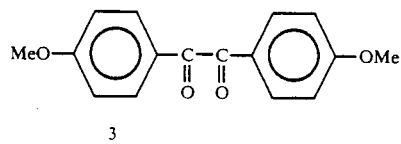

27.2 g (0.2 mol) of 4-methoxybenzaldehyde (1) in ca. 100 ml of ethanol was added to a solution of 10 g of potassium cyanide in 20 ml of water. The reaction mixture was refluxed for 1.5 hours and cooled down. Crude 4,4'-dimethoxybenzoin (2) was recrystallized from ethanol. Pure 2 was obtained (14.2 g, 52.2 % yield).

A mixture of 27.5 g of copper sulfate (0.11 mol), 25 g of pyridine and 10 g of water was heated until the copper sulfate was completely dissolved. Then, 13.5 g of 2 (0.05 mol) was added, and the heating was continued for 2 hours.

Figure 8:
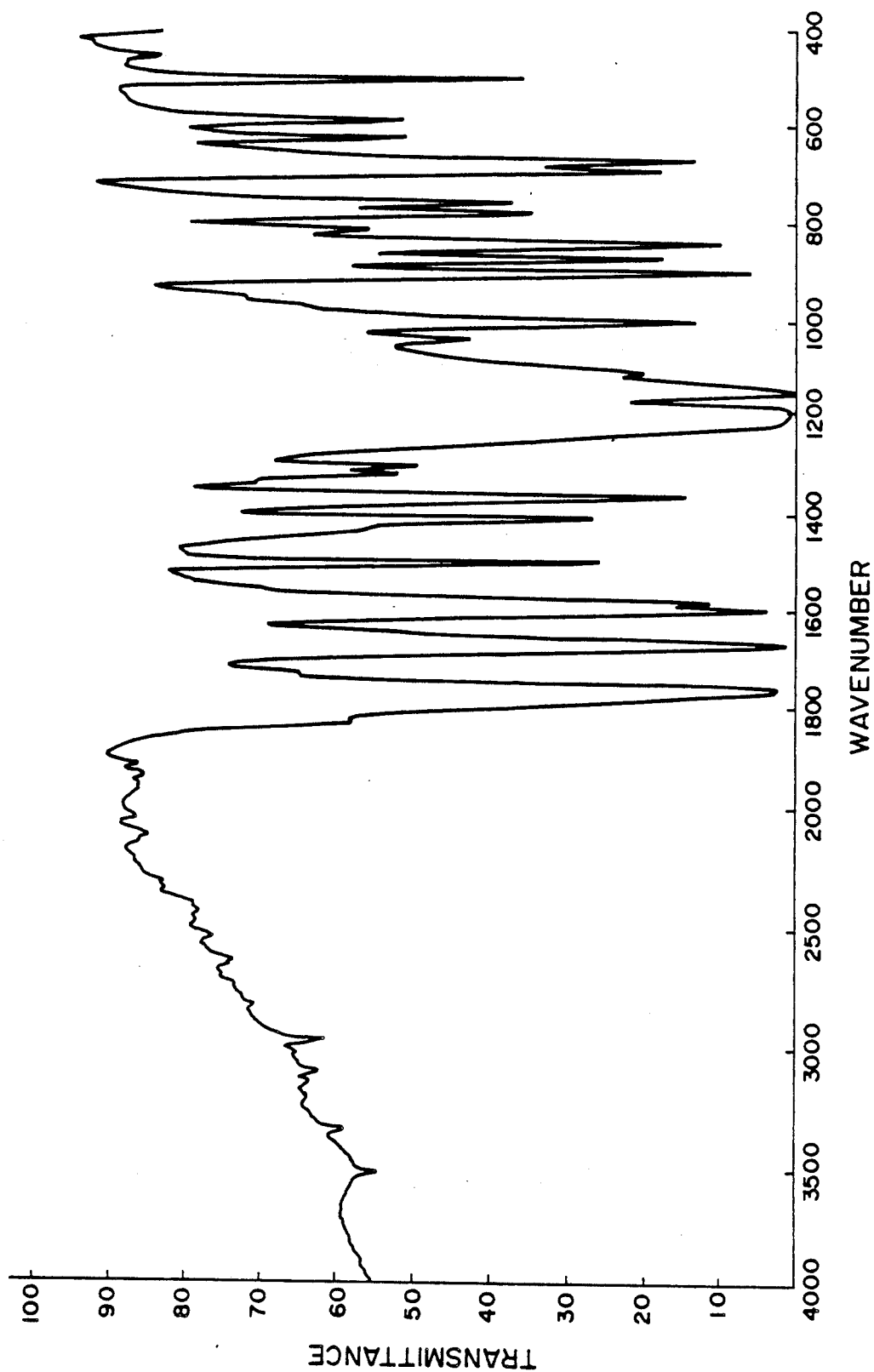
FIG. 8 through FIG. 12 are reproduction of IR charts.

After cooling, the copper-sulfate-pyridine solution was decanted and the crude benzil 3 was washed with water, and then heated with 50 ml of 10% hydrochloric acid. After cooling, the crude benzil 3 was filtered and recrystallized from ethanol. Pure benzil 3 was obtained (9.26 g, 68.8% yield).

m.p.: 130.5–131.5° C.
Elementary analysis
Found: C 71.07%, H 5.23%.
Calcd. (71.10%) (5.22%).
IR spectrum is shown in FIG. 8.

According to the same method as described above, the following compounds could be obtained.

Figure 9:
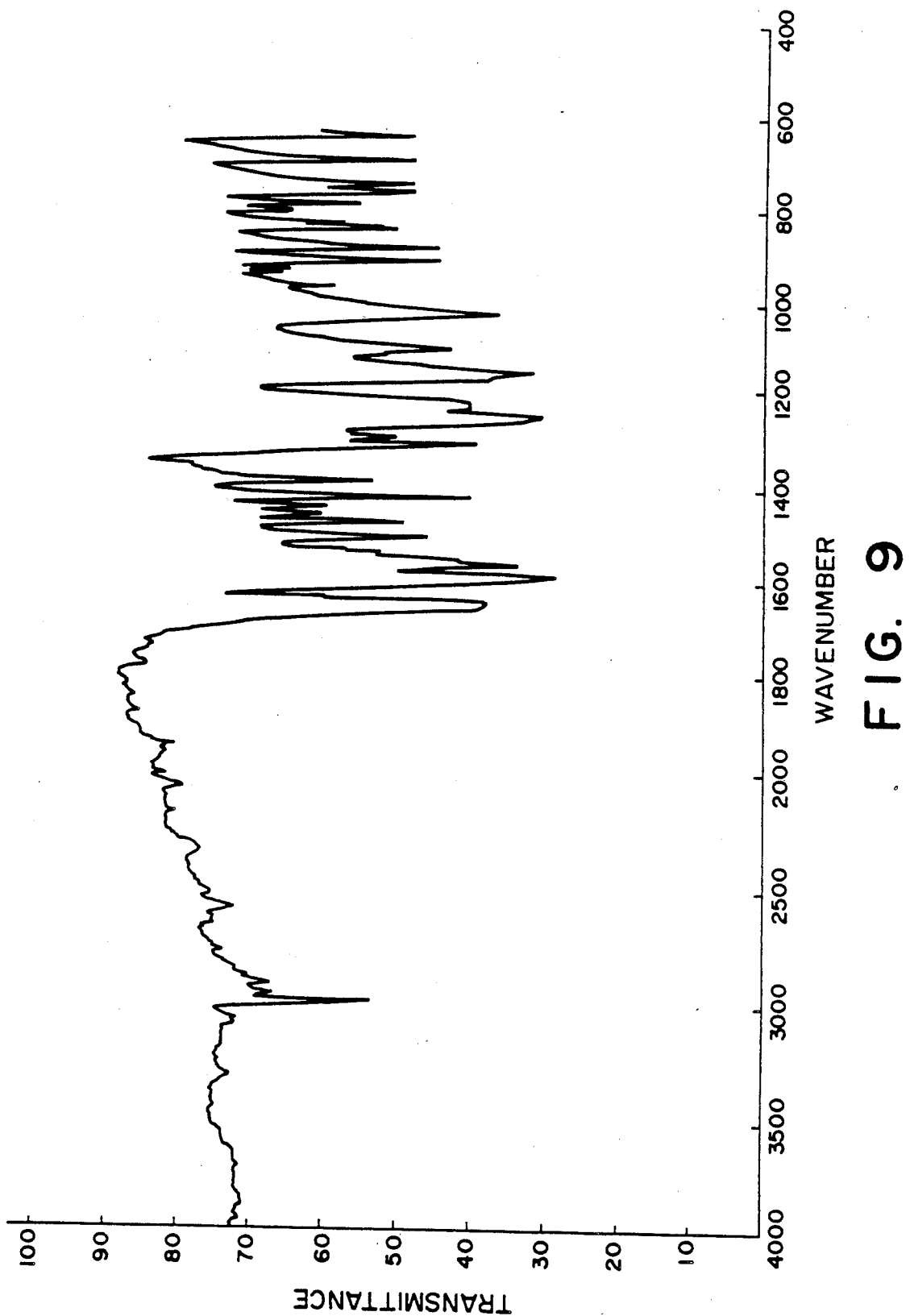

4,4'-diethoxybenzil:
m.p. 150–151° C.
Elementary analysis: Found: C 72.48 %, H 6.04 %. Calcd. (72.47%), (6.08%)
IR spectrum is shown in FIG. 9.

Figure 10:
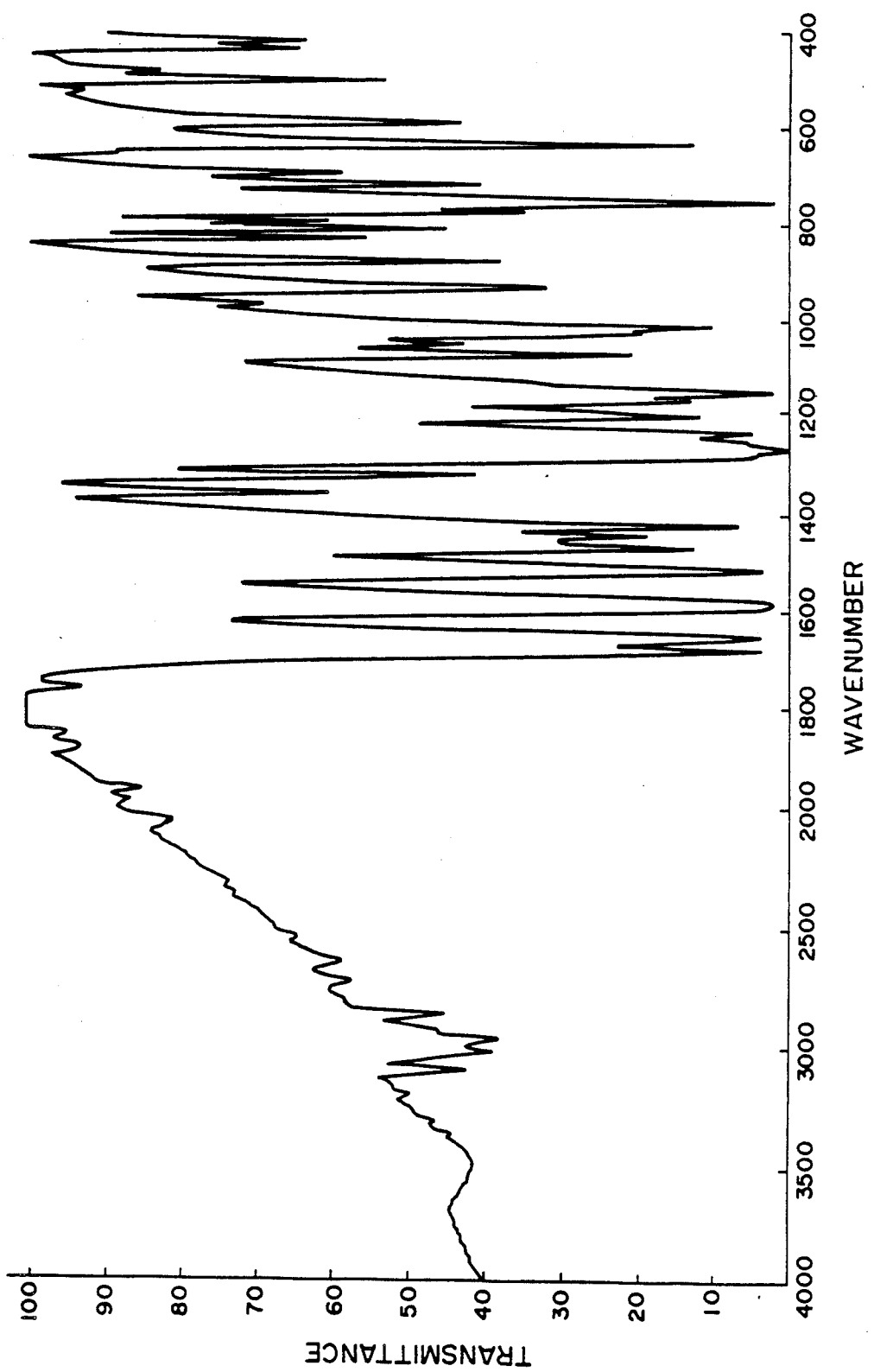

2-chloro-3',4'-dimethoxybenzil
m.P 113–115° C.
Elementary analysis: Found: C 63.03%, H 4.34%. Calcd. (63.07%), (4.30%)
IR spectrum is shown in FIG. 10.

Also, 4,4'-dihydroxybenzil was obtained by changing the methoxy groups in 4,4'-dimethoxybenzil to hydroxy groups by use of hydrobromic acid.

Figure 11:
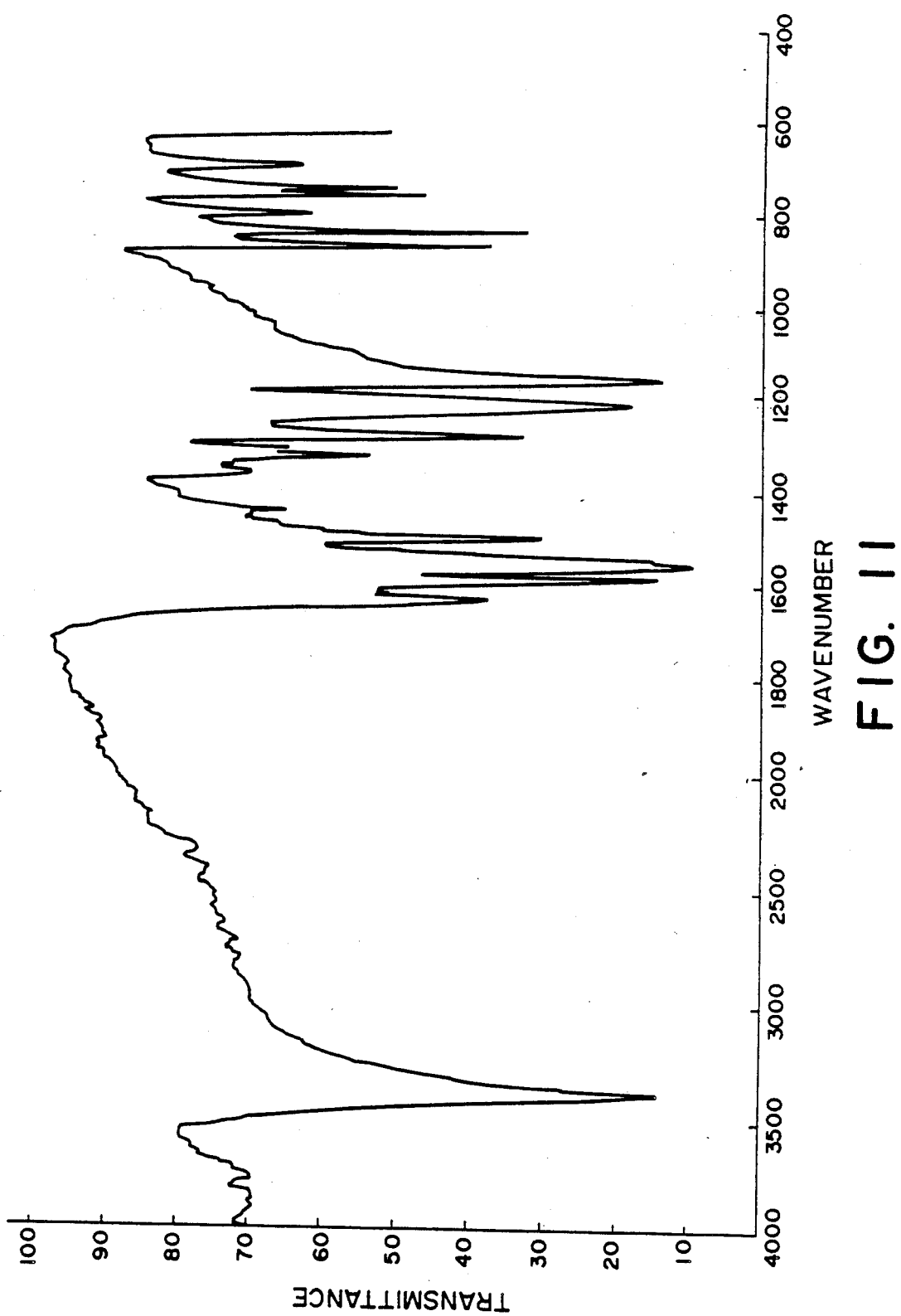

4,4'-dihydroxybenzil:
m.p. 250–253° C.
Elementary analysis Found: C 69.44%, H 4.20%
Calcd. (69.42%) (4.16%)
IR spectrum is shown in FIG. 11.

Further, from 4,4'-dihydroxybenzil, 4,4'-diacetoxybenzil was obtained with acetic anhydride. 4,4'-diacetoxybenzil:
m.p. 85–87° C.

Figure 12:
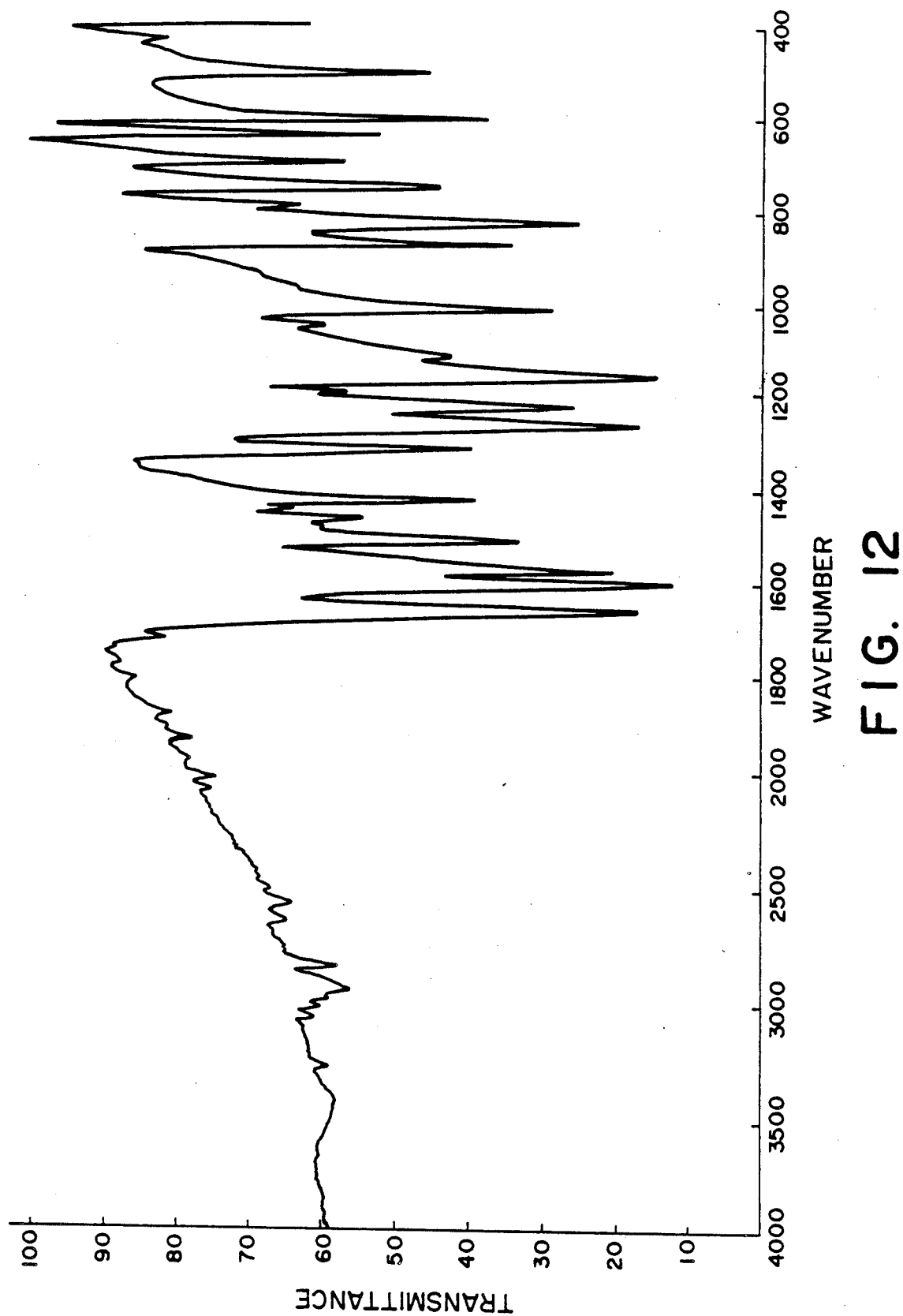
Figure 13:
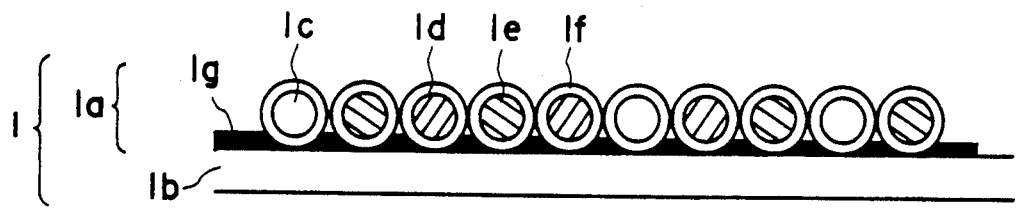
FIG. 13 is a side view showing an embodiment of the recording medium of the present invention.

Elementary analysis Found: C 66.28%, H 4.36% Calcd. (66.26%), (4.32%)
IR spectrum is shown in FIG. 12.

The compound represented by the formula (I) may be sometimes further improved in sensitivity when used together with an amine. As the amine to be used in combination, aromatic amines may include ethyl-p-dimethylaminobenzoate, isoamyl-p-dimethylaminobenzoate, phenyl-p-dimethylaminobenzoate, ethyl-p-diethylaminobenzoate, phenyl-p-diethylaminobenzoate, N,N-dimethylaniline, N,N-diethylaniline, N,N-dimethylbenzylamine, N-benzyl-N-methylaniline, N,N-dibenzylaniline, triphenylamine and the like.

Examples of aliphatic amines may include trimethylamine, triethylamine, tripropylamine, dimethylcyclohexylamine, triethanolamine and the like.

Examples of polyamines may include methylenediamine, hexamethylenediamine, 1,4-cyclohexanediamine, phenylenediamine and the like.

The amines as mentioned above may be used either alone or as a mixture of two or more species. Also, the photopolymerization initiator of the formula (I) can be used in the range of about 1:5 to about 1:1000, preferably about 1:10 to about 1:100, respectively by weight, relative to the polymerizable compound having an unsaturated double bond as described later.

Next, the photopolymerization initiator in the image-forming element (B) will be described. The photopolymerization initiator in the element (B) has the maximum absorption in the range of 360 to 430 nm. The absorption maximum as mentioned in the present invention refers to the maximum peak in the range of wavelength of 300 nm or longer when the absorbance of the photopolymerization initiator is measured in chloroform. When the photopolymerization initiator is a complex system, the absorption maximum refers to a peak having a greater absorption. The photopolymerization initiator in the element (B) may for example be a thioxantone derivative or a complex system comprising a compound selected from the group (a) shown below and a compound selected from the group (b) shown below, but the present invention is not limited thereto.

Group (a):

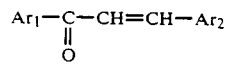

and coumaine derivatives;

Group (b): S-triazine derivatives having at least one trihalomethyl group, and camphor quinone.

As the thioxanthone derivative, thioxanthone, 2-chlorothioxanthone, isopropylthioxanthone, 2,4-diethylthioxanthone, 2,4-diisopropylthioxanthone or the compound of the following formula (II) as disclosed in Japanese Laid-Open Pat. Application No. 154970/1980 are preferred:

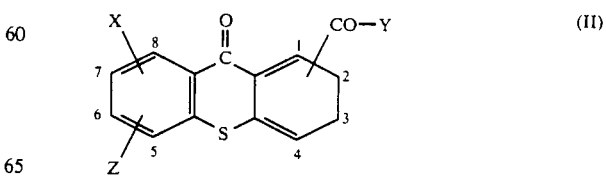

wherein X represents hydrogen, halogen, —CN, —OH, —SH, —NH₂, —NO₂, —SO₃H, phenylsulfonyl, or alkylsulfonyl, alkyl, alkoxy, alkylthio, alkylamino, dialkylamino, or —CO-alkyl group having 1 to 4 carbon atoms in each alkyl moiety, or further —CO—OR$_1$, —CO—SR$_1$, —CO—N (R$_1$)(R$_2$), —CO-piperidyl, —CO-pyrrolidinyl or —CO-morpholinyl group; Z means hydrogen, —OH, —SH, or alkyl, alkoxy, alkylthio or dialkylamino group having 1 to 4 carbon atoms in each alkyl moiety; Y represents —OR$_1$—, —SR$_1$, N(R$_1$)(R$_2$), piperidyl, pyrrolidinyl or morpholino group; R$_1$ represents alkyl group having 1 to 24 carbon atoms, alkoxyalkyl group having 3 to 10 carbon atoms, C$_5$-C$_6$ cycloalkyl group, phenyl group, naphthyl group, —(CH$_2$)$_m$-phenyl group or —(CH$_2$CH$_2$O)$_n$—CH$_3$ group; R$_2$ means hydrogen or one residue of R$_1$; is an integer of 1 or 2; n is an integer of 2 to 10; with proviso that at least one of X and Z is not hydrogen when the above group of —CO—Y— is in the 4-position and Y means —OCH$_3$.

The thioxanthone derivative may also be improved in sensitivity when used in combination with the above amines The thioxanthone compound can be used in the range of about 1:5 to about 1:1000, preferably, about 1:10 to about 1:100, respectively be weight, relative to the polymerizable compound having an unsaturated double bond as described below.

As the compound of the group (a), the compounds represented by the formula and having the maximum absorptions at 360 nm to 430 nm may be included:

(wherein Ar'$_1$ and Ar'$_2$ are each aromatic ring or heterocyclic ring, and at least one of the Ar'$_1$ and Ar'$_2$ has an N atom-containing group. Ar'$_1$ and Ar'$_2$ may be either identical or different).

Specific examples may include the following compounds:

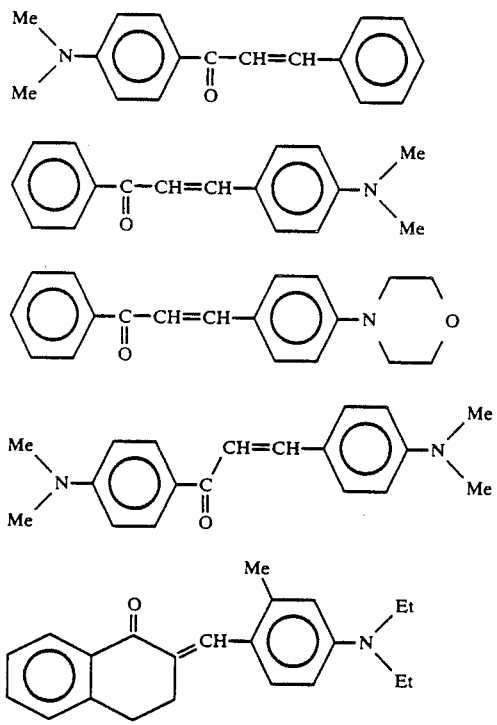

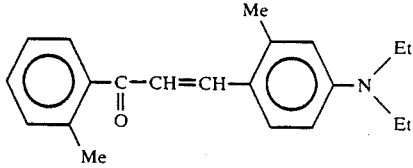

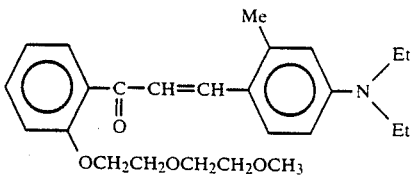

OCH$_2$CH$_2$OCH$_2$CH$_2$OCH$_3$

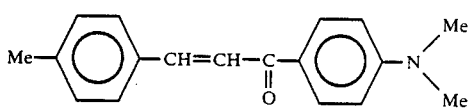

Examples of the coumarine derivatives of the group (a) may include 4-methyl-7-hydroxycoumarine, 4-methyl-7-dimethylaminocoumarine, 4-methyl-7-ethylaminocoumarine, 4-methylpiperidino[3.2-g]coumarine, 4-methyl-7-cyclohexylaminocoumarine, 4-trifluoromethyl-7-diethylaminocoumarine, 3-phenyl-4-methyl-7-diethylaminocoumarine, 3-(2'-N-methylbenzimidazoyl)-7-diethylaminocoumarine, 4-trifluoromethyl-6-methyl-7-ethylaminocoumarine, 3-phenyl-7-aminocoumarine, cyclopenta[C]dijulolidino[9,10-e]-11H-pyran-11-one, 10-trifluoromethyljulolidino[9,10-e]-11H-pyran-11-one, 9-methyljulolidino[9,10-e]-11H-pyran-11-one, 4-trifluoromethyjulolidino[9,10-e ]-11H-pyran-11-one, 4-trifluoromethyl-N-ethylpiperidino[3,2-g]coumarine, or compounds having maximum absorptions in the range of about 360 nm to about 430 nm among the coumarine derivatives disclosed in Japanese Patent Publication No. 42684/1984.

Specifically, there may be included 3,3'-carbonylbis(7-methoxycoumarine), 5,7-dimethoxy-3,3'-carbonylbiscoumarine, 5,7,7'-trimethoxy-3,3'-carbonylbiscoumarine, 3,3'-carbonylbis(5,7-dimethoxycoumarine), 3-benzoyl-7-diethylaminocoumarine, 7-diethylamino-3-(4-dimethylaminobenzoyl)coumarine, 7-diethylaminothienoylcoumarine and the like.

Also, the photopolymerization initiator comprising a compound selected from the group (a) and a compound selected from the group (b), may be used in combination with the above amines.

Examples of the S-triazine derivative having at least one trihalomethyl group of the group (b) may include 2-phenyl-4,6-bis(trichloromethyl)-S-triazine, 2-(p-chlorophenyl)-4,6-bis(trichloromethyl)-S-triazine, 2-(p-tolyl)-4,6-bis(trichloromethyl)-S-triazine, 2-(p-methoxyphenyl)-4,6-bis(trichloromethyl)-S-triazine, 2-(2',4'-dichlorophenyl)-4,6-bis(trichloro-methyl)-S-triazine, 2,4,6-tris(trichloromethyl)-S-triazine, 2-methyl-4,6-bis(-trichloromethyl)-S-triazine, 2-n-nonyl-4,6-bis(trichloromethyl)-S-triazine, 2-(α,α,β-trichloroethyl)-4,6-bis(trichloromethyl)-S-triazine, 2-styryl-4,6-bis(trichloromethyl)-S-triazine, 2-(p-methylstyryl)-4,6-bis(trichloromethyl)-S-triazine, 2-(p-mcthoxystyryl)-4,6-bis(-trichloromethyl)-S-triazine, 2-methyl-4,6-bis(tribromomethyl)-S-triazine, 2,4,6-tris(tribromomethyl)-S-triazine, 2,4,6-tris(dibromo-methyl)-S-triazine, 2-amino-4-methyl-6-tribromomethyl-S-triazine, 2-methoxy-4-methyl-6-trichloromethyl-S-triazine and the like.

Also, the photopolymerization initiator comprising a combination of the compounds selected from the group (a) and the group (b) may be used in an amount ranging from about 1:5 to about 1:1000, preferably from about 1:10 to about 1:100, relative to the polymerizable compound having an unsaturated double bond as described below.

Next, the photopolymerization initiator in the image-forming element (C) will be described. Such a polymerization initiator is a compound having the maximum absorption at 430 nm or longer. The maximum absorption of the above photopolymerization initiator should be preferably at 700 nm or shorter, further 600 nm or shorter. When the polymerization initiator is a complex system, a peak having a greater absorption is taken.

As such a photopolymerization initiator, photopolymerization initiators of the complex system comprising a compound selected from the group (c) shown below and a compound selected from the above group (b) may be included, but the present invention is not limited thereto Group (c): compounds of the following formula (IV) and compounds having a maximum absorption at about 430 nm or longer among coumarine derivatives:

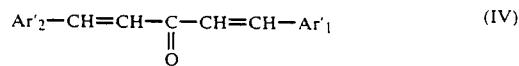

(wherein $Ar'_1$ and $Ar'_2$ are the same as in the formula (III)).

Specific examples of the formula (IV) may include the following compounds:

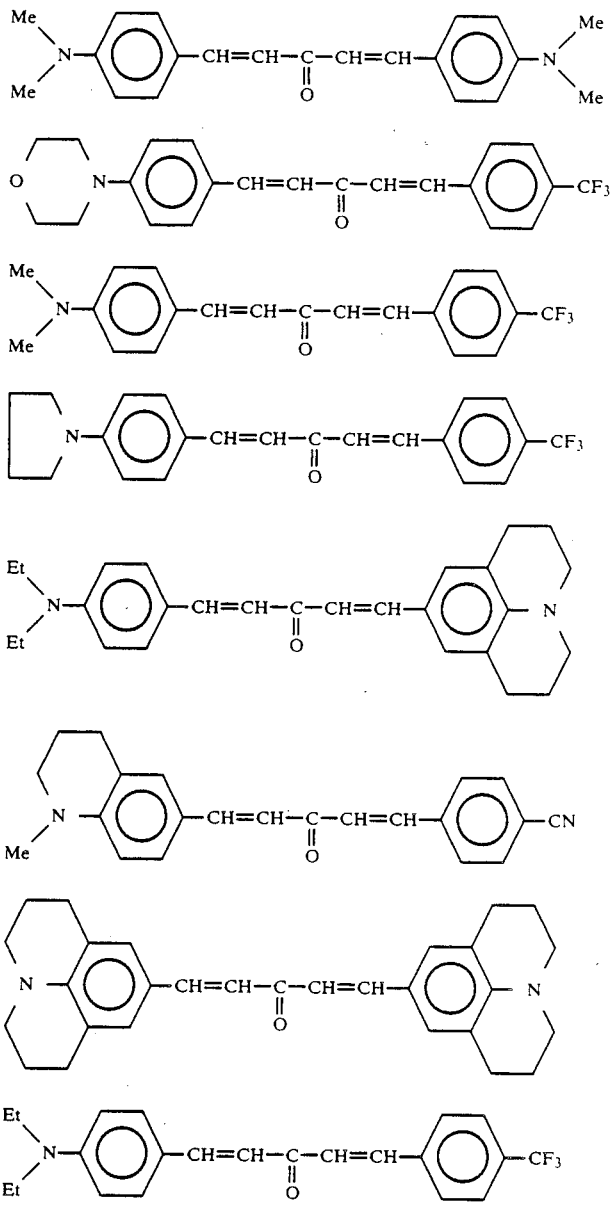

Examples of the coumarine derivatives of the group (c) may include-3-(3'-benzthiazolyl)-7-diethylaminocoumarine or coumarine derivatives disclosed in Japanese Patent Publication No. 42684/1984 having the maximum absorption at about 430 nm or longer.

Specific examples may include 7-diethylamino-3,3'-carbonylbiscoumarine, 3,3'-carbonylbis(7-diethylaminocoumarine), 9-(7-diethylamino-3-coumarinoyl)-1,2,4,5-tetrahydro-3H, 6H,10H[1]benzopyrano[9,9a,1-gh]-quinolazin-10-one, 9,9'-carbonylbis(1,2,4,5-tetra-hydro-3H,6H,10H[1]benzopyrano-[9,9a,1-gh]quinofurazin-10-one, 10-acetyljulolidino[9,10-e]-11H-pyran-11-one, 10-cyanojulolidino[9,1-e]-11H-pyran-11-one, 10-carboxyjulolidino [9,10-e]-11H-pyran-11-one.

The above amines may be also added to the photopolymerization initiator comprising a compound selected from the group (c) and a compound selected from the group (b).

Also, the photopolymerization initiator comprising the combination of the compounds selected from the group (c) and the group (b) may be used in an amount ranging from about 1:5 to about 1:1000, preferably from about 1:10 to about 1:100, respectively by weight, relative to the polymerizable compound having unsaturated bond as described above. The compound of the group (c) and the compound of the group (b) may be used at a ratio ranging from about 1:10 to about 10:1.

The polymerizable compound having an unsaturated double bond in the above elements (A), (B) and (C) refers to a compound having at least one unsaturated double bond in its chemical structure in the form of monomer, oligomer or polymer. Its examples may include monomers such as methyl acrylate, methyl methacrylate, acrylonitrile, acrylamide, etc.; esters of unsaturated carboxylic acids such as acrylic acid, methacrylic acid, itaconic acid, crotonic acid, isocrotonic acid, maleic acid and the like with aliphatic polyhydric polyol compounds such as ethylene glycol, triethylene glycol, tetraethylene glycol, trimethylolpropane, 1,3-butane diol, pentaerythritol, dipentaerythritol, and the like; further urethane acrylates, urethane methacrylates synthesized by the polycondensation reaction of polyisocyanates (which may have been reacted with polyols, if necessary) with alcohols, amines containing an unsaturated bond; and epoxy acrylates and polyester acrylates, synthesized by the addition reaction of epoxy resins with acrylic acid or methacrylic acid, spinacrylates, etc.

Also, as the polymer, there may be included those having a skeletone of polyalkyl, polyether, polyester, polyurethane, etc. in the main chain and having introduced polymerizable or crosslinkable reactive groups, typically acrylic group, methacrylic group, cinnamoyl group, cinnamylideneacetyl group, furylacryloyl group, cinnamic ester, etc., but the present invention is not limited to these.

Also, the image-forming elements (A), (B) and (C) containing the photopolymerization initiator and the polymerizable compound having an unsaturated double bond as described above can further contain additives such as known binders, colorants, UV-absorbers, plasticizers, thermal polymerization inhibitors, etc.

Examples of the binder polymer may include polyalkyl acrylates such as polymethyl acrylate, polyethyl acrylate and the like; polyalkyl methacrylates such as polymethyl methacrylate, polyethyl methacrylate and the like; methacrylic acid copolymers, acrylic acid copolymers, maleic acid copolymers; chlorinated polyolefins such as chlorinated polyethylene, chlorinated polypropylene and the like; polyvinyl chloride, polyvinylidene chloride, polyacrylonitrile or copolymers of these; polyvinyl alkyl ether, polyethylene, polypropylene, polystyrene, polyamide, polyurethane, chlorinated rubber, cellulose derivatives, polyvinyl alcohol, polyvinyl pyrrolidone, etc., but the present invention is not limited to these.

These polymers may be used either singly or as a mixture of two or more kinds at a suitable ratio. Also, as the binder, waxes which may be either compatible or noncompatible may be used. These polymers can be mixed in any desired amount in the whole composition The colorant is a component to be contained for forming an optically recognizable image, and various pigments and dyes can be suitably used. Examples of such pigments, dyes may include inorganic pigments such as carbon black, yellow lead, molybdenum red, blood red, etc.; organic pigments such as Hansa Yellow, Benzidine Yellow, Brilliant Carmine 6B, Lake Red C, Permanent Red F5R, Phthalocyanine Blue, Victoria Blue Lake, Fast Sky Blue, etc ; leuco dyes, phthalocyanine dyes, etc Also, a color forming agent which is colored through the reaction with the developer after image formation may be also used. The amount of the colorant may be preferably 0.1 to 30 parts by weight based on the whole composition.

As the UV-absorber, there may be included benzophenone type, salicylate type, benzotriazole type, oxalic acid anilide type compounds may be included. Also, the UV-ray absorber can be combined suitably with the above photopolymerization initiator to narrow the photosensitive wavelength region of the photopolymerization initiator, thereby enabling smaller overlapping of the photosensitive wavelength regions of the photopolymerization initiators.

Examples of the plasticizer may include phthalates such as dimethyl phthalate, diethyl phthalate and the like; glycol esters such as dimethyl glycol phthalate, methylphthalethyl glycolate and the like; phosphates such as triphenyl phosphate and the like; aliphatic dibasic acid esters such as dioctyl adipate, dioctyl azelate, dibutyl maleate and the like.

As the thermal polymerization inhibitor, there are p-methoxyphenol, hydroquinone, t-butylcatechol, cuprous chloride, 2,6-di-t-butyl-p-cresol, organic acid copper, etc. Next, the image-forming elements (A), (B) and (C) comprising the components as described above are physically or chemically bound onto a support as particulate elements with particle sizes of about 3 to about 50 μm, preferably 7 to 15 μm in the case of solids, or even in the case where the elements (A), (B) and (C) may be liquid or solid, as microcapsules with particle sizes of about 3 to about 50 μm, preferably 7 to 15 μm. The average particle size of the elements (A), (B) and (C) should preferably be around 10 μm. When the microcapsules are bound onto the support with an adhesive, the adhesive to be used may include those of various types, such as epoxy polyvinyl alcohol, polyvinyl pyrrolidone, polyacrylamide, polyester, urethane type, acrylic, urethaneacrylic, and ethylenevinyl acetate copolymer type adhesives. Here, when the elements (A), (B) and (C) are carried in particulate form on a support, for preventing inhibition of photopolymerization by oxygen, it is desirable to provide further an oxidation preventive layer such as a transparent film.

As the microencapsulation method, there may be applied any of the known methods, such as the simple coacervation method, the complex coacervation method, the interfacial polymerization method, the in-situ polymerization method, the interfacial precipitation method, the phaseseparation method, the spray drying method, the in-air suspension coating method, the Nakano Chemical method, etc.

As the support, polyester, polycarbonate, triacetyl cellulose, nylon polyimide, polyethylene terephthalate, aluminum, etc may be employed, and these may be in shape of film, plate, drum or sphere.

The recording medium of the present invention can be applied to the image-forming method disclosed in U.S. Pat. No. 4,399,209 as described above, but here is described about a particularly preferable imageforming method by use of the recording medium of the present invention. The image-forming method was developed by our research group (U.S Pat. Application Ser. No. 869,689, filed June 2, 1986), and plural kinds of energies including light are imparted to the recording medium of the present invention corresponding to given image recording information, and the transfer characteristic is changed by imparting at least one of the energies imagewise. This transfer characteristic is determined as desired depending on the kind of the transfer recording medium used. For example, in the case of a transfer recording medium wherein the image is transferred in the thermally molten state, it is melting point, softening point or glass transition point, while in the case of a transfer recording medium wherein the image is transferred under sticky state or the state penetrable into the transferreceiving medium, it is viscosity at the same temperature. Also, the plural kinds of energies to be used for formation of transfer image may be determined as desired depending on the kinds of the transfer recording medium used For example, photoelectron beam, heat, pressure, etc. may be used in suitable combination. As the particularly preferable change in these physical properties, the transfer image should be preferably transferred under sticky state or the state penetrable into the transfer-receiving medium. This is because the transfer image forming energy for obtaining transferred image corresponding to the recording information is the lowest among the abovementioned methods to give the image amplification effect during image formation by transfer, whereby recording speed can be improved to a great extent. Our research group has further proposed a recording method with respect to fixing of the above recording method (U.S. Ser. No. 927,876, filed Nov. 7, 1986), a recording method utilizing a vaporizable dye (U.S. Ser. No. 070,194, filed July 6, 1987).

A preferable image-forming method for providing the recording medium of the present invention for image formation is to be described. For understanding of this method, description is made about an example by use of a recording medium in which transfer image is formed with light and heat energies by referring to FIGS. 1A to 1D.

Figure 1B:
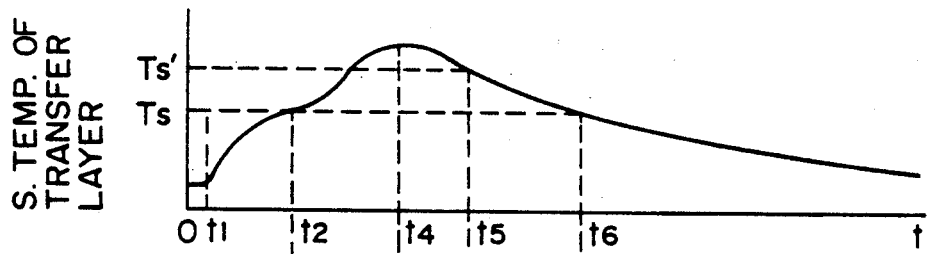
Figure 1C:
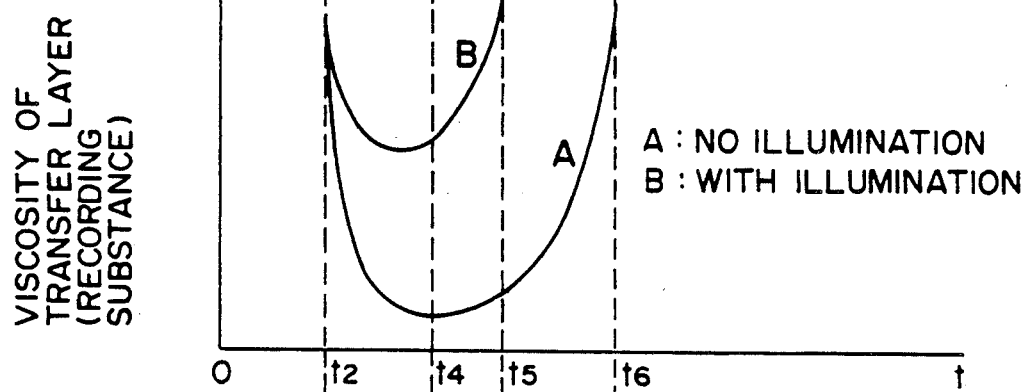
Figure 1D:
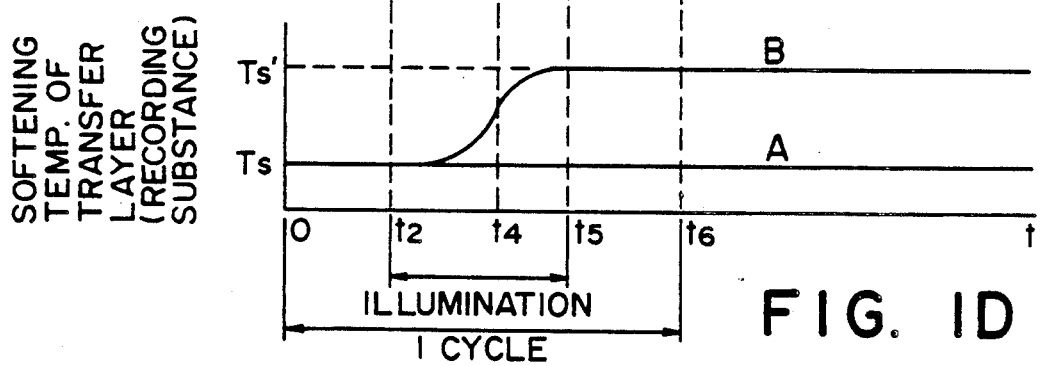

The time axis (axis of abscissa) of each graph in FIGS. 1A–1D corresponds to one another. Also, in the transfer recording layer are contained the image-forming elements (A), (B) and (C). FIG. 1A shows how the surface temperature of the heating means is elevated when the heating means such as a thermal head, etc. is driven for heat generation for the time of $0-t_3$ and thereafter dropped. The transfer recording medium in pressure contact against the heating means will exhibit the temperature change as shown in FIG. 1B with the temperature change of the heating means, namely elevated in temperature with a time delay of $t_1$, reaches the maximum temperature at the time $t_4$ similarly with a delay after $t_3$, and thereafter dropped in temperature. The recording layer has a softening temperature Ts, and will be abruptly softened in a temperature region of Ts or higher to be reduced in viscosity. This behavior is shown by the curve A in FIG. 1C. After reaching Ts at the time $t_2$, viscosity drop continues up to the time $t_4$ where the maximum temperature is reached, and the viscosity will be again increased simultaneously with lowering in temperature until the time $t_6$ when the temperature is dropped to Ts. In this case, the physical properties of the transfer recording layer are not basically subject to change in physical properties as before the heating, and the layer exhibits a reduction in viscosity similarly as described above when heated to a temperature of Ts or higher Therefore, if heating necessary for transfer in pressure contact against the transfer-receiving medium, for example, to a temperature of Ta or higher is effected, the transfer recording layer will be transferred for the same reason as the transfer mechanism similarly as the heat transfer recording of the prior art. However, in the case of the present invention, when light is irradiated simultaneously with heating from the time $t_2$ as shown in FIG. 1D, the transfer recording layer will be softened to activate the photopolymerization initiator contained in the transfer recording layer and, if the temperature is elevated enough to make the reaction rate greater, the probability of polymerization of the polymerizable monomer will become dramatically greater, whereby curing or hardening will proceed abruptly.

When heating and photoirradiation are effected simultaneously, the transfer recording layer exhibits the behaviors as shown by the curve B in FIG. 1C. And, with the progress of the reaction, the softening temperature is elevated to be changed from Ts to Ts' at the time $t_5$ when polymerization or crosslinking is completed. This is shown in FIG. 1D. Accordingly, when heating is effected in the subsequent transfer step, a difference in property occurs between the portion changed to Ts' and the portion unchanged. Accompanied with this change, the transfer initiation temperature Ta which is the temperature at which the transfer recording layer initiates transfer is also changed to become Ta'. Accordingly, for example, if heating is effected to Tr satisfying Ta<Tr<Ta', only the portion where softening temperature is not elevated is transferred onto the transfer-receiving medium. Although depending on the temperature stability precision of the transfer step, the Ts'-Ts at this time should be preferably about 20° C. or higher Particularly, 40° C. or higher is preferable. This value is the same in the case of Ts>Ts'. Thus, by controlling heating or nonheating, transfer image can be formed by effecting photoirradiation at the same time.

The transfer initiation temperature in the present invention is measured as described below.

A 6 μ-thick transfer recording layer formed on a 6 μ-thick polyethylene terephthalate (PET) film is caused to contact 0.2 mm-thick wood-free paper as a transfer-receiving medium having a surface smoothness (Bekk smoothness) of 50–200 seconds The resultant laminate of the transfer recording medium and the paper is passed at a rate of 2.5 mm/sec between a pair of rollers as follows. The first roller is a hollow cylindrical iron roller of 40 mm diameter in which a 300 W-halogen lamp heater is stored and is disposed on the side of the transfer recording medium. The second roller disposed on the side of the paper comprises a similar iron roller of 40 mm diameter coated with a 0.5 mm-thick fluorine rubber layer. The two rollers are operated to exert a linear pressure of 4 kg/cm. In the measurement, the surface temperature of the first roller is measured by a temperature sensor, e.g., a thermistor, while controlling the halogen lamp heater to provide a prescribed temperature At a time of 4 seconds after the laminate is passed through the two rollers, the transfer recording medium 5 is peeled off the paper moved horizontally at a peeling angle of about 90° and at a rate equal to the conveying speed of the rollers, so that it is observed whether the transfer recording layer has been transferred onto the paper. The operation is continued while gradually raising the surface temperature of the first roller (at a rate of 10° C./min or less), and the minimum temperature at which the transfer starts to occur effectively (as identified by saturation of a transferred image density) is identified as the transfer initiation temperature of the transfer recording medium or the transfer recording layer.

Here, the change in transfer characteristic is described as a change in the softening temperature Ts, but since the recording medium of the present invention obtain a recorded in the later transfer step, the change may be in the sticky state or the penetration state onto the transfer-receiving medium, and can be adapted if there is no change in Ts as described above. As understood here, when the recording medium of the present invention is used for the above image-forming method, the image-forming elements in the recording medium are required to be solid at least normal temperature.

As the plural kinds of energies to be used for formation of the transfer image, a combination of light and heat or an energy convertible to heat selected from electric ultrasonic and pressure energies is preferable in energy efficiency.

Further, by use of the recording medium of the present invention and light sources conforming to the wavelength regions of the respective photopolymerization initiators in the elements (A), (B) and (C) for the above image-forming method, multi-color images can be formed.

FIGS. 2A-2D are schematic partial sectional views showing a relationship between a transfer recording medium and a thermal head according to the present invention. In this embodiment, a heat energy modulated according to a recording signal is applied in combination with a light energy selected depending on the color of an image forming element of which the transfer characteristic is intended to be changed Herein, "modulation" is an operation of changing a position to which the energy is applied corresponding to a given image signal, and "in combination" covers a case where the light energy and the heat energy are applied simultaneously as well as a case where the light energy and the heat energy are applied separately.

A transfer recording medium 1 shown in FIGS. 2A-2D comprises a transfer recording layer 1a disposed on a base film 1b. The transfer recording layer 1a is formed as a layer of distributed particulate image forming elements. Respective image forming elements show different color tones. In the embodiment shown in FIGS. 2A-2D, for example, each image forming element contains any one colorant selected from magenta (M), cyan (C) and yellow (Y). The colorants to be contained in the image forming elements, however, are not restricted to magenta, cyan and yellow, but may be colorants of any color depending on an intended use. Each image forming element contains in addition to a colorant, a functional or sensitive component, of which the transfer characteristic changes when light and heat energies are applied thereto. The image forming elements may be formed on the substrate 1b together with a binder or by heat-melting the above components.

The functional component in the image forming elements has a wavelength dependency depending on the colorant contained. More specifically, an image forming element (M) containing a magenta colorant causes polymerization to be hardened or cured when a heat flux and a light beam with a wavelength (M) are applied thereto. Similarly, an image forming element (C) containing a cyan colorant and an image forming element (Y) containing a yellow colorant respectively cause polymerization to be hardened when a heat and a light beam with a wavelength $\lambda(C)$ and heat, and a light beam with a wavelength $\lambda(Y)$ and heat, respectively, are applied thereto. A cured or hardened image forming element does not cause decrease in viscosity even when heated in a subsequent transfer step, so that it is not transferred to a transfer-receiving medium. The heat and light are applied corresponding to an information signal to be recorded.

In this way, the transfer recording medium is superposed on a thermal head 14, and light is illuminated so as to cover the entire heat generation region of the thermal head 14. The wavelengths of the illumination light are so selected sequentially as to react on image forming elements (M), (C) and (Y) to be illuminated. For example, if image forming elements (M), (C) and (Y) to be illuminated are colored in any one of magenta, cyan and yellow, light beams having a wavelength $\lambda(M)$, $\lambda(C)$ and $\lambda(Y)$, respectively, are successively irradiated.

More specifically, while the transfer recording medium is illuminated with a light beam having a wavelength $\lambda(M)$, resistance heating elements 14b, and 14c, for example, of the thermal head are caused to generate heat. As a result, among the image forming elements (M) containing a magenta colorant, those applied with the heat and the light beam with a wavelength $\lambda(M)$ are cured as shown by hatching in FIG. 2A (in FIGS. 2B, et seq., the cured elements are also indicated by hatching).

Figure 2A:
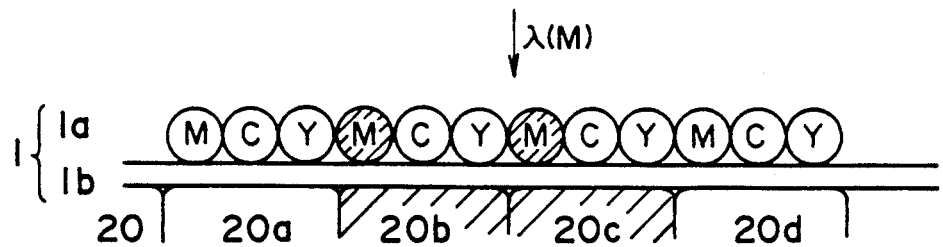
FIGS. 2A through 2D illustrate a method for forming multi-color transfer image by use of the recording medium of the present invention.
Figure 2B:
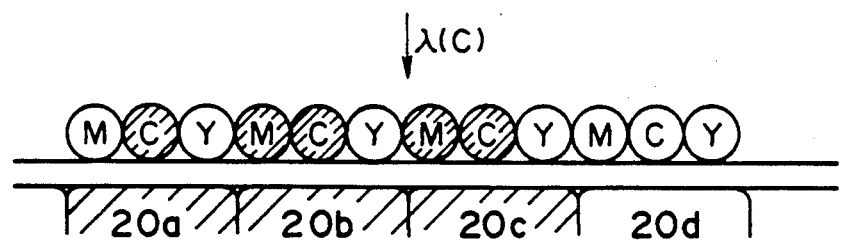

Then, as shown in FIG. 2B, while the transfer recording layer 1a is illuminated with a light beam with a wavelength $\lambda(C)$, resistance heating elements 20a, 20b and 20c in a thermal head 20 are caused to generate heat, whereby among the image forming elements containing a cyan colorant, those applied with the heat and the light beam with a wavelength $\lambda(C)$ are cured. Further, as shown in FIG. 3C, while the light flux with wavelength $\lambda(Y)$ is provided, resistance heating elements 14c and 14d are caused to generate heat, whereby among the image forming elements (y), those applied with the heat and the light beam with a wavelength (Y) are cured to finally leave a transferable image formed of non-cured image forming elements in the transfer recording layer 1a. The transferable image is then transferred to a transfer-receiving medium 10 in a subsequent transfer step as shown in FIG. 2D.

In the transfer step, the transfer recording medium on which the transferable image has been formed is caused to contact the transfer-receiving medium 10 through the faces and heat is applied from the transfer recording medium side or the transfer-receiving medium 10 side, whereby the transferable image is selectively transferred to the transfer-receiving medium 10 to form a visible image thereon. Accordingly, the heating temperature in the transfer step is so determined in connection with the change in transfer characteristics that the transferable image is selectively transferred. Further, in order to effectively carry out the transfer, it is also effective to apply a pressure simultaneously. The pressurization is particularly effective when a transfer-receiving medium having a low surface smoothness is used. Further, where the physical property controlling a transfer characteristic is a viscosity at room temperature, the pressurization alone is sufficient to effect the transfer.

The heating in the transfer step is suitable for producing a durable multi-color image with a stability and an excellent storability.

In the above embodiment explained with reference to FIGS. 2A to 2D, the entire area of the thermal head 20 is illuminated with light while resistance heating elements of the thermal head 20 are selectively energized. On the contrary, while a certain area of the transfer recording medium are uniformly heated, e.g., by energizing all the resistance heating elements of the thermal head 20 shown in FIGS. 2A-2D, light illumination may be effected selectively or imagewise to form a similar multi-color image. More specifically, light energy having a wavelength modulated according to a recording signal and selected depending on the color of an image forming element of which the transfer characteristic is intended to be changed, is imparted along with heat energy.

Figure 3A:
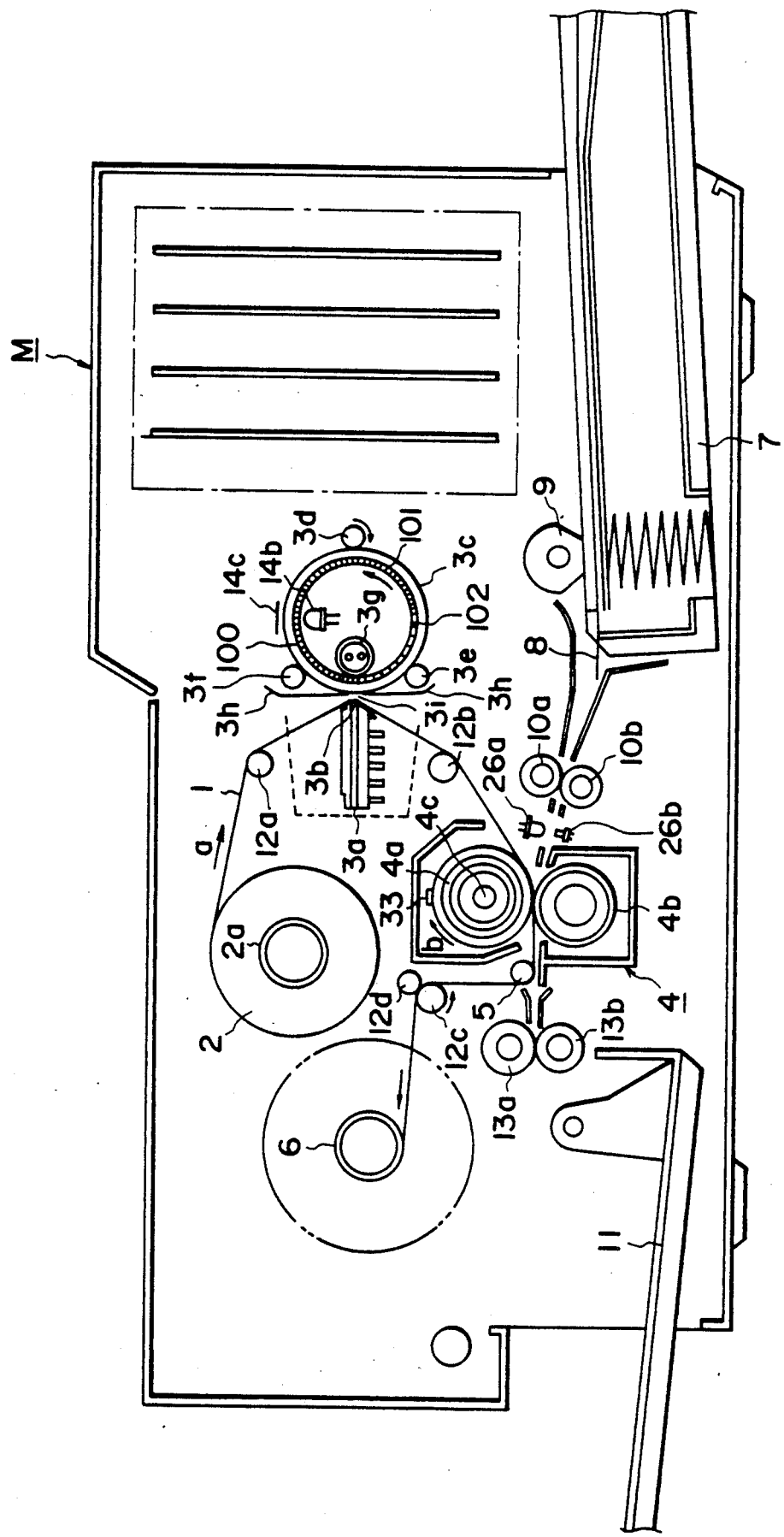
FIG. 3 is a side view showing the inner portion of an embodiment of the recording apparatus of the present invention.
Figure 3B:
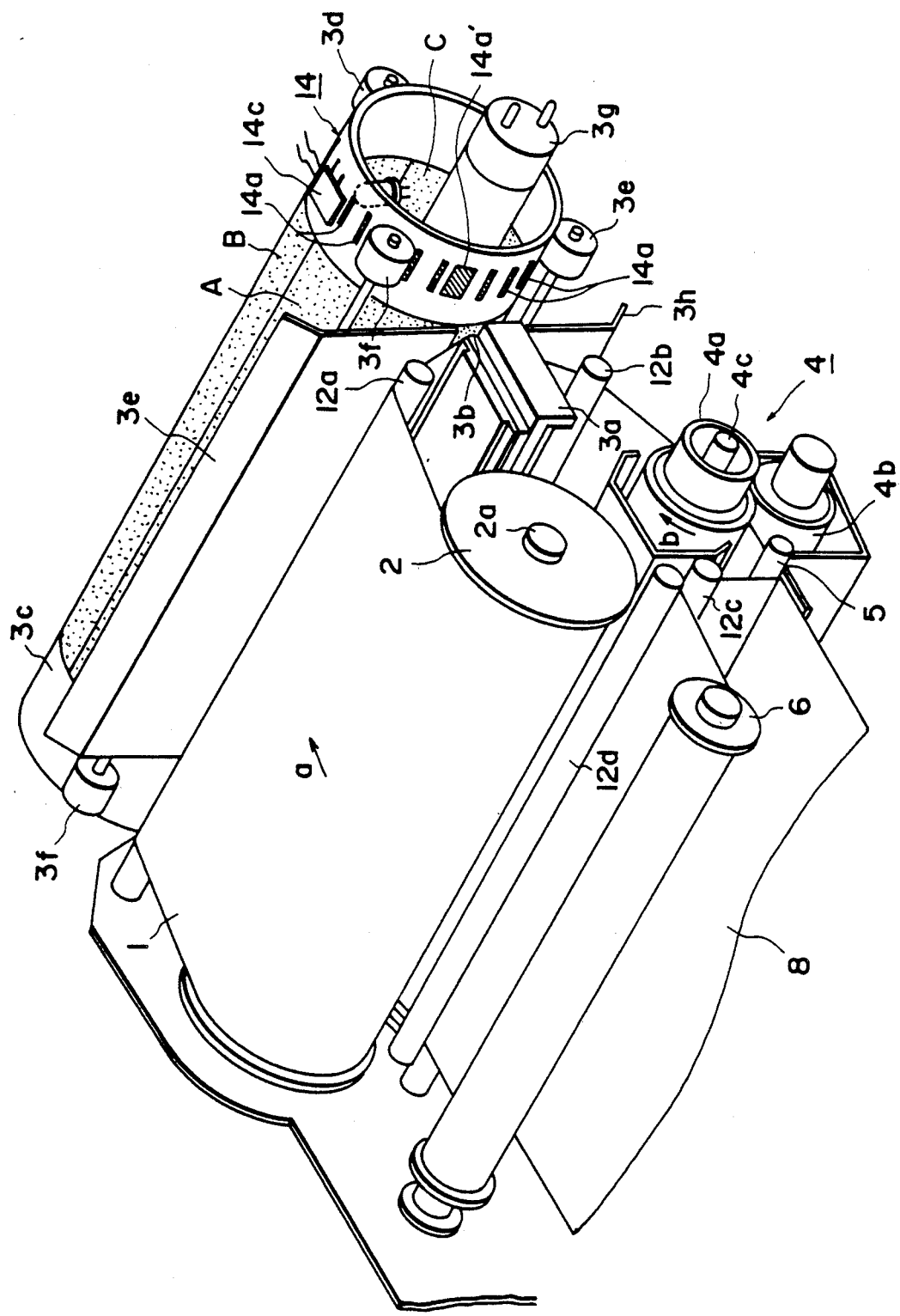

By use of FIGS. 3A and 3B, a preferable example of the recording apparatus using the recording medium of the present invention is to be described.

In the Figures, reference numeral 1 denotes a transfer recording medium of the present invention in shape of an elongated sheet, which is wound up in a roll and assembled detachably in an apparatus body M as a feed roll 2. Thus, the feed roll 2 is detachably mounted on the freely rotatable shaft 2a provided in the apparatus M.

Now, the leading end of the transfer recording medium 1 is passed from the feed roll 2 via a guide roller 12a, a recording head 3a and a guide roller 12b, diverted from between a transfer roller 4a and a pressure roller 4 with guide rollers 12c and 12d to reach a wind-up roller 6, and the leading end is fixed on the wind-up roller 6 by engaging with a means such as gripper (not shown). Thereafter, while giving the wind-up roller 6 a torque in the direction of an arrow c by means of a known driving means, the transfer recording medium 1 is delivered in the arrow direction a, whereby it is successively wound up around the circumferential surface of the wind-up roller 6.

The feed roll 2 during the above feeding operation is given a predetermined tension by, for example, a hysteresis brake (not shown), and by the tension and the above guide rollers 12a, 12b, the transferred recording medium 1 is constituted so as to be conveyed with pressure contact under predetermined pressure and angle against the recording head 3.

The recording section is constituted of a heating means for imparting heat energy to the recording medium 1 and a photoirradiation means for imparting photoenergy similarly to the transfer recording medium 1.

The heating means comprises an arrangement of an array of heat-generating elements 3b of the line type for A-4 size with, for example, a width of 0.2 mm and 8 dots/mm, which generate heat corresponding to given image signals, are disposed on the surface of the recording head 3a and are constituted so that the support 1b side of the transfer recording medium 1 may be pressure contacted under a predetermined pressure due to a backward tension during conveying against the above heat-generating element array 3b. The above image signals are emitted from the controlling section of, for example, a facsimile recorder, image scanner, or electronic blackboard, depending on the use.

Figure 4:
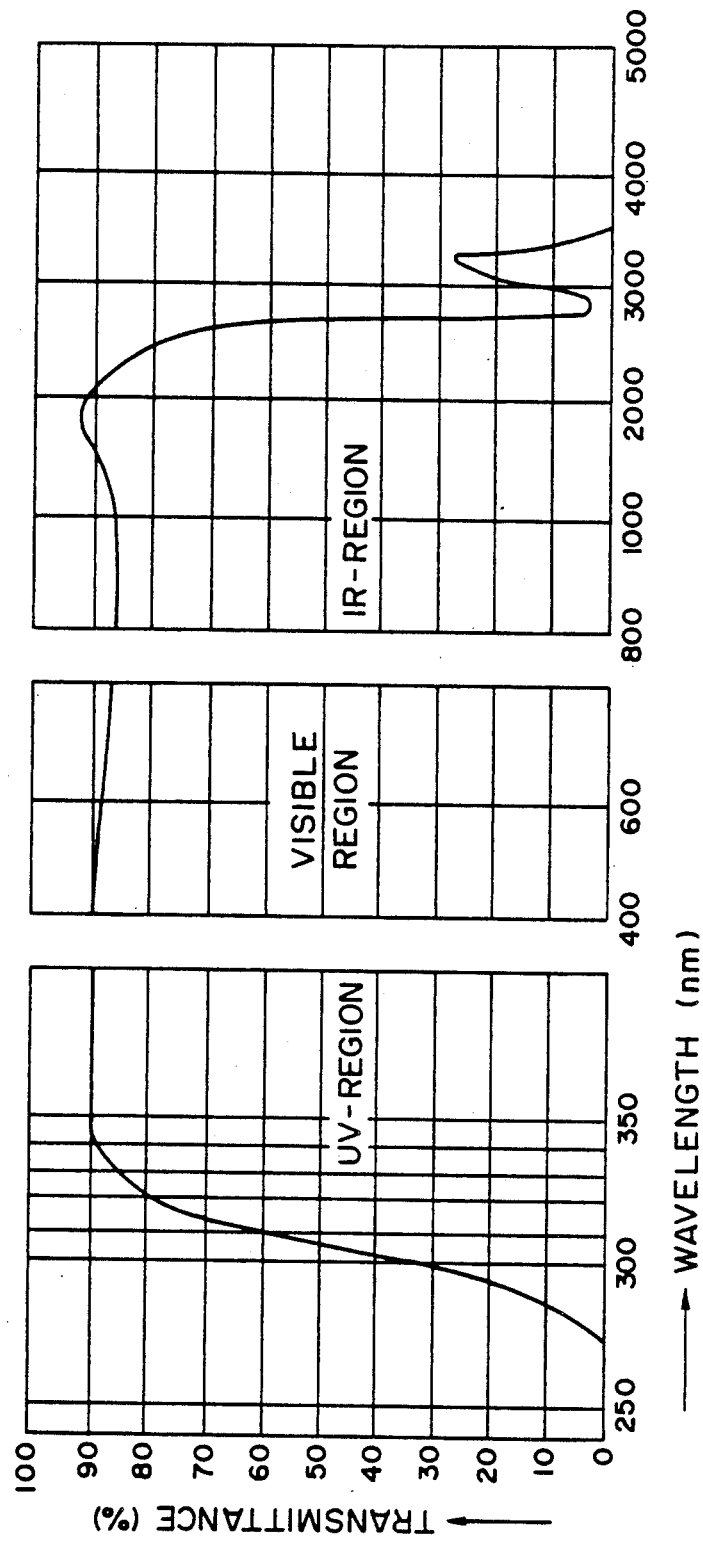
FIG. 4 is a perspective view showing only the inner portion of the recording apparatus shown in FIG. 3.

On the other hand, on the transfer recording layer 1a side opposite to the above recording head 3a is provided a light irradiation means. As the light irradiation means, three fluorescent lamps with different emitting wavelength regions and capable of causing individually the reaction of the elements (A), (B) and (C) respectively (e.g., FL10A70E35/33T15 (peak wavelength 335 nm, produced by Toshiba K.K.), FL10A70E39/33T15 (peak wavelength 390 nm, produced by Toshiba K.K.), FL10A70B/33T15 (peak wavelength 450 nm, produced by Toshiba)) may be employed, but as shown in FIGS. 3A and 3B, a rotatory member 3c comprising a cylinder made of a glass with a thickness of 2 mm (DURAN 50, produced by SCHOTT Co., West Germany) having a spectral transmittance characteristic as shown in FIG. 4 may be rotatably supported with three opposing roller pairs 3d, 3e and 3f and rotated at a constant speed by driving the above roller 3d with a motor.

The above rotatory member 3c is coated with three kinds of phosphors 100, 101 and 102 on the inner surface at 120° (at three equally divided portions) in the circumferential direction. These phosphors 100, 101 and 102 are excited by the light from a light source (e.g., a sterilization lamp GL-20, produced by Toshiba K.K.) disposed within the rotatory member 3c to emit fluorescence.

The fluorescence emitted from the phosphor 100 must be one which permits only the element (A) to react efficiently, and has substantially no influence on the elements (B) and (C). The fluorescence emitted from the phosphors 101, 102 must be also those which will permit only the element (B) or the only the element (C), respectively, to react efficiently. As mentioned also previously, the wavelength region for permitting the photopolymerization initiator to react may be preferably in the range of 300 to 600 nm, but in the case of performing recording by use of three colors of cyan, magenta and yellow, further division of the range of 300 to 600 nm into the three wavelength regions at about 360 nm and about 430 nm is most preferred in view of the kind of the photopolymerization initiator and the kind of phosphor, whereby cross-talk can be prevented. When the wavelength region is divided further into the three regions at 360 nm and 430 nm, the light rays from the above phosphors 100, 101 and 102 are required to have peak wavelengths of the spectral distribution in the ranges of 300 to 360 nm, 360 to 430 nm and 430 to 600 nm, respectively, for preventing cross-talk. When the wavelength region of 300 to 600 nm is divided as described above, the light emitted from the phosphor 100 can permit only the element (A) to react efficiently, giving substantially no influence on the elements (B) and (C), and similarly the light emitted from the phosphor 101 can permit only the element (B) and the light emitted from the phosphor 102 only the element (C) to react efficiently.

As the phosphor 100 having the peak wavelength in the wavelength region of 300 to 360 nm, one composed mainly of thallium-activated calcium phosphate (Ca(PO$_4$)$_2$:Tl) or thallium-activated calcium zinc phosphate ((Ca·Zn)$_3$(PO$_4$)$_2$:Tl$^+$) is preferred. These phosphor materials have a high emission strength and are very preferable.

As the phosphor 101 having the peak wavelength in the wavelength region of 360 nm to 430 nm, one composed mainly of europium-activated strontium magnesium pyrophosphate ((Sr,Mg)$_2$P$_2$O$_7$·Eu) is preferred.

As the phosphor 102 having the peak wavelength in the wavelength region of 430 to 600 nm, one composed mainly of europium-activated barium magnesium aluminate (Ba,MgAl$_{16}$O$_{27}$:Eu) is preferred.

Figure 5:
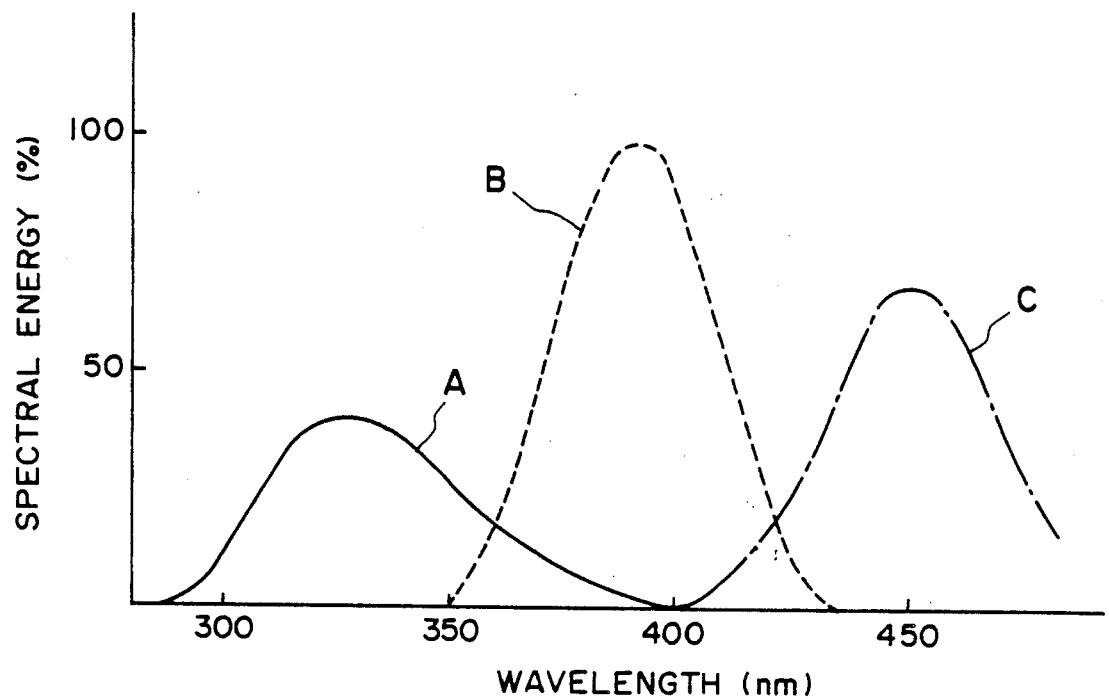
FIG. 5 is a graph showing an example of the light transmittance characteristic of a glass used for the rotatory member 3c shown in FIG. 3.

As can be seen from FIG. 5, the peak wavelengths of the respective phosphors A, B and C exist in the range of 300 to 360 nm, in the range of 360 to 430 nm and in the range of 430 nm to 600 nm, respectively. For example, thallium-activated calcium phosphate has the peak wavelength at 335 nm (graph A), europium-activated strontium magnesium pyrophosphate at 395 nm (graph B) and europium-activated barium magnesium aluminate at 453 nm, respectively.

In the phosphors of 100, 101 and 102, in addition to the above materials, other additives may be mixed, but it is preferred that 50 % by weight or more, particularly 80 % by weight or more, based on each of the phosphors 100, 101 and 102 should comprise a material emitting fluorescence as described above.

The light emitted by the above phosphors 100, 101, 102 passes through the slit 3i (slit width is, for example, 0.5 mm) to irradiate the transfer recording layer 1a.

Accordingly, when the light is irradiated from the light source 3g with rotation of the above rotatory member 3c, the phosphors 100, 101 and 102 are successively excited to be emitted, whereby lights with different spectral distributions from each other will be irradiated successively through the slit 3i onto the transfer recording layer 1a.

Here, description is made about the system for controlling the rotational speed and the phase of the above rotatory member 3c.

The above rotatory member 3c, as shown in FIG. 3B, has a large number of light intercepting portions 14a at a constant pitch in a stripe on the circumference near the edge portion, and one light intercepting portion 14a' among them is formed with a broader width than the other light intercepting portions 14a. Also, innerside of the rotatory member 3c is disposed a light emitting member 14b so as to sandwich the above light intercepting portions 14a therebetween, and a light receiving member 14c such as a photodiode is disposed on the outside.

Figure 6A:
FIG. 6 is an example of the signal of the light receiving member for detecting rotation of the rotatory member 3c and its integrated waveform.

With the above structure, under the state where the rotatory member 3c is under rotation at a constant speed, the signals obtained from the light receiving member 14c becomes as shown in FIG. 6A The level "LOW" shown in FIG. 6A is the state when the light from the emitting member 14b transmits through the rotatory member 3c and is received at the light receiving member 14c, and the level "HGH" is the state where the light is intercepted with the light intercepting member 14a and not received at the light receiving member 14c. Accordingly, since the frequency of the leading edge of the signal appears as the rotational speed of the rotatory member 3c, it becomes possible to control the rotational speed of the rotatory member 3c by detecting and controlling this signal.

Figure 6B:

Next, in controlling the phase, the integrated waveform of the above FIG. 6A may assume a shape as shown in FIG. 6B, and due to the broader width of one of the light intercepting portions 14a (14a'), the peak value of the integrated waveform becomes higher at that portion. Therefore, based on the point of time at which the peak value becomes higher as the reference, a yellow line-synchronized signal, a magenta line-synchronized signal, a cyan line-synchronized signal and other signals as will be described herein-after may be prepared and controlled.

Next, the transfer section 4 is to be described. The transfer section 4 is disposed on the downstream side of the above recording section 3 in the conveying direction of the transfer recording medium 1 and is constituted, as shown in FIG. 3, of a transfer roller 4a driven to rotate in the direction of an arrow b, and a pressure roller 4b pressed against the transfer roller 4a.

The above transfer roller 4a is constituted of an aluminum roller covered with a silicone rubber with a thickness of 1 mm and a hardness of 70° and maintained at a surface temperature of 90° to 100° C. with a built-in halogen lamp of 800 W.

On the other hand, the pressure roller 4b is composed of an aluminum roller covered with a 1 mm-thick silicone rubber with a hardness of 70°, and the pressing force between the pressure roller 4b and the transfer roller 4a is set by a pressing means (not shown) such as a spring, etc. at 6 to 7 kgf/cm.

Further, the recording paper 8 which is the transfer-receiving medium loaded within the cassette 7 is fed by the feeding roller 9, a register roller pair 10a, 10b and the leading end of the recording paper 8 is detected by a register sensor 26 comprising an LED 26a and a phototransistor 26b to control the feeding time, whereby the recording paper is fed to the transfer section in synchronism so as to be superposed on the image region of the above transfer recording medium 1.

Next, the recording method by use of the recording apparatus as constituted above is to be described.

In this example, heat is selectively applied corresponding to given image signals and light is imparted uniformly.

By driving a motor, the transfer recording medium 1 is successively delivered from the feed roll 2, and light and heat are imparted corresponding to the image signals onto the transfer recording layer 1a of the transfer recording medium 1 at the recording section, whereby images are formed. The above transfer recording layer 1a, when imparted with light of a certain wavelength and heat, is elevated in softening temperature, that is, changed irreversibly in its transfer characteristic, thus assuming a state of non-transfer onto the recording paper 8.

Figure 7:
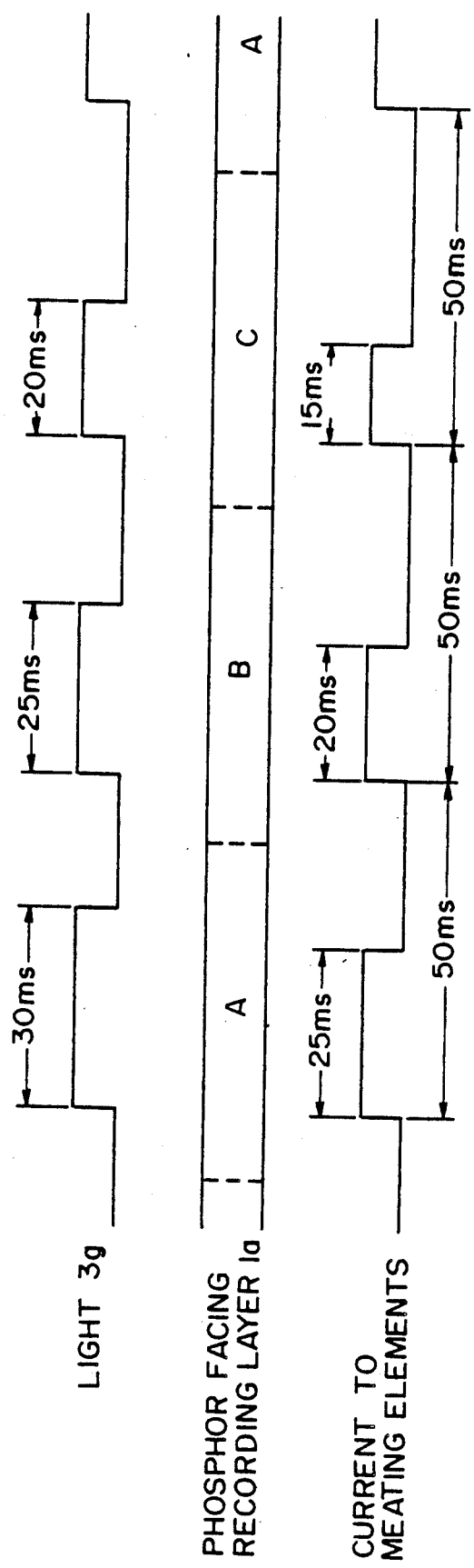
FIG. 7 and FIG. 17 are timing charts for imparting light and heat.

Therefore, as shown in the timing chart in FIG. 7, for magenta color recording, a current is supplied for 25 ms to a portion of heating elements 3b corresponding to the image signals of the complementary color of magenta, namely the image signals of green color, and at the same time the light source 3g is turned on for 30 ms. At this time, to the transfer recording 1a positioned at the slit 3i is opposed the phosphor A of the rotatory member 3c, and a photoenergy with a spectral distribution represented by a curve A in FIG. 5 is uniformly imparted to the transfer recording layer 1a.

Next, for cyan color recording, from 50 ms after initiation of current supply to the heatgenerating elements in the above magenta color recording, a current is supplied for 20 ms to a portion of the heat-generating elements 3b corresponding to the image signal of complementary color of cyan, namely red color, and at the same time the light source 3g is turned on for 25 ms. At this time, to the transfer recording layer 1a positioned at the slit 3i is opposed the phosphor B of the rotatory member 3c, whereby a photoenergy with a spectral distribution represented by the curve B in FIG. 5 is uniformly imparted to the transfer recording layer 1a.

Next, for yellow color recording, from 50 ms after initiation of current supply to the heat generating elements in the above cyan color recording, a current is supplied for 15 ms to a portion of the heat-generating elements 3b corresponding to the image signal of complementary color of yellow, namely blue color, and at the same time the light source 3g is turned on for 20 ms. At this time, to the transfer recording layer 1a positioned at the slit 3i is opposed the phosphor C of the rotatory member 3c, whereby a photoenergy with the spectral distribution represented by a curve C in FIG. 5 is uniformly irradiated onto the transfer recording layer 1a.

In the manner as described above, corresponding to the image signals of the complementary colors of yellow, magenta and cyan, heat generation of the recording head 3a, rotation of the rotatory member 3c and energization of the light source 3g are controlled to form a transfer image on the transfer recording layer 1a, which is conveyed onto the transfer recording medium 1 in synchronism at a repetition cycle of 150 ms/line.

As described above, in the recording medium of the present invention, a recording material is used in which the above photopolymerization initiator in the element (A) constituting the recording layer is a compound represented by the following formula (I):

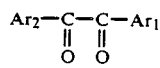

(wherein $Ar_1$, $Ar_2$ each represent aromatic ring, heterocyclic ring which may have substituent, and may be either the same or different), and the above photopolymerization in the element (B) has the maximum absorption in the range of 360 to 430 nm, and also the above photopolymerization initiator in the element (C) has the maximum absorption in the range of 430 nm or longer. Thus, when the recording medium of the present invention is used for the multi-color image recording method, the image-forming elements involve little overlapping of the sensitive wavelength regions, so that a sharp multi-color image can be obtained, even by use of light sources such as fluorescent lamps with different emission wavelength regions as such, without irradiation of a light in an extremely narrow wavelength region by a filter with low transparency such as a band-pass filter, etc.

Also, the recording apparatus divides the sensitive wavelength region further into the three wavelength regions at about 360 nm and 430 nm, and a phosphor composed mainly or thallium-activated calcium phosphate or thallium-activated calcium zinc phosphate having a strong light-emitting intensity is used as the phosphor having the peak wavelength in the wavelength region of 300 to 360 nm, and therefore it involves little liability of cross-talk and can give a sharp multi-color recorded image.

The present invention is described below by referring to Examples Here, description is made by referring to the method in which multi-color images are formed by photoenergy and heat energy as described above.

EXAMPLE 1

TABLE 1

| Category | Components | wt. % |
|---|---|---|
| Polymerizable component | Reaction product of p-cyclo-hexyldiisocyanate and hydroxy-propyl acrylate | 60 |
| Binder | Chlorinated polyethylene | 30 |
| Photopolymerization initiator | 4,4'-Dimethoxybenzil | 1.5 |
| Amine | Ethyl-p-dimethylaminobenzoate | 1.5 |
| Colorant | Brilliant Carmine 6B-NS (produced by Toyo Ink K.K.) | 7 |

TABLE 2

| Category | Components | wt. % |
|---|---|---|
| Polymerizable component | Reaction product of p-cyclo-hexyldiisocyanate and hydroxy-propyl acrylate | 62 |
| Binder | Chlorinated polyethylene | 30 |
| Photopolymerization initiator | 2-Chlorothioxanthone | 1.5 |
| Amine | Phenyl-p-diethylaminobenzoate | 1.5 |
| Colorant | Cyanine Blue RNF (produced by Toyo Ink K.K.) | 5 |

TABLE 3

| Category | Components | wt. % |
|---|---|---|
| Polymerizable component | Reaction product of p-cyclo-hexyldiisocyanate and hydroxy-propyl acrylate | 62 |
| Binder | Chlorinated polyethylene | 30 |
| Photopolymerization initiator | 3,3'-Carbonylbis(7-diethyl-aminocouramine, | 1.5 |
| | Tris-2,4,6-(trichloromethyl)-S-triazine | 1.5 |
| Colorant | Lionol Yellow SS-OW (produced by Toyo Ink K.K.) | 5 |

First, a mixture of 10 g of the components shown in Table 1 and 20 parts by weight of methylene chloride was mixed into 200 ml of water containing a surfactant with a HLB value of at least 10 such as cationic or nonionic surfactant and 1 gl of gelatin dissolved therein, and emulsified by stirring at 8,000 to 10,000 rpm by means of a homomixer under warming at 60° C. to obtain oil droplets with an average particle size of 26 μm.

Further, stirring was continued at 60° C. for 30 minutes to evaporate methylene chloride, thereby to provide an average particle size of 10 μm. Into the dispersion 20 ml of water containing 1 g of gum arabic dissolved therein was added, and by adding NH₄OH (ammonia) water while under cooling slowly, pH was adjusted to 11 to give a microcapsule slurry, followed by slow addition of 1.0 ml of aqueous 20 % glutaraldehyde solution to harden the capsule walls. Then, solid-liquid separation was effected by Nutsche filter, followed by drying in a vacuum dryer at 35° C. for 10 hours to obtain an image-forming element (A) in the form of microcapsule. Similarly, an element (B) was obtained from the components in Table 2 and an element (C) from the components in Table 3. The image-forming elements thus obtained were microcapsules with the cores 1c, 1d and 1e being covered with shells 1f, having particle sizes of 7 to 15 μm, with an average particle size of about 10 μm.

The image-forming elements (A), (B) and (C) formed as described above were bonded onto a support 1b comprising a polyethyleneterephthalate film with a thickness of 6 μm with the use of an adhesive 1g formed by applying a composition comprising several droplets/100 cc of a surfactant dropped into an aqueous 5 % PVA solution, to form a transfer recording layer 1a, thus constituting a transfer recording medium 1.

Figure 14:
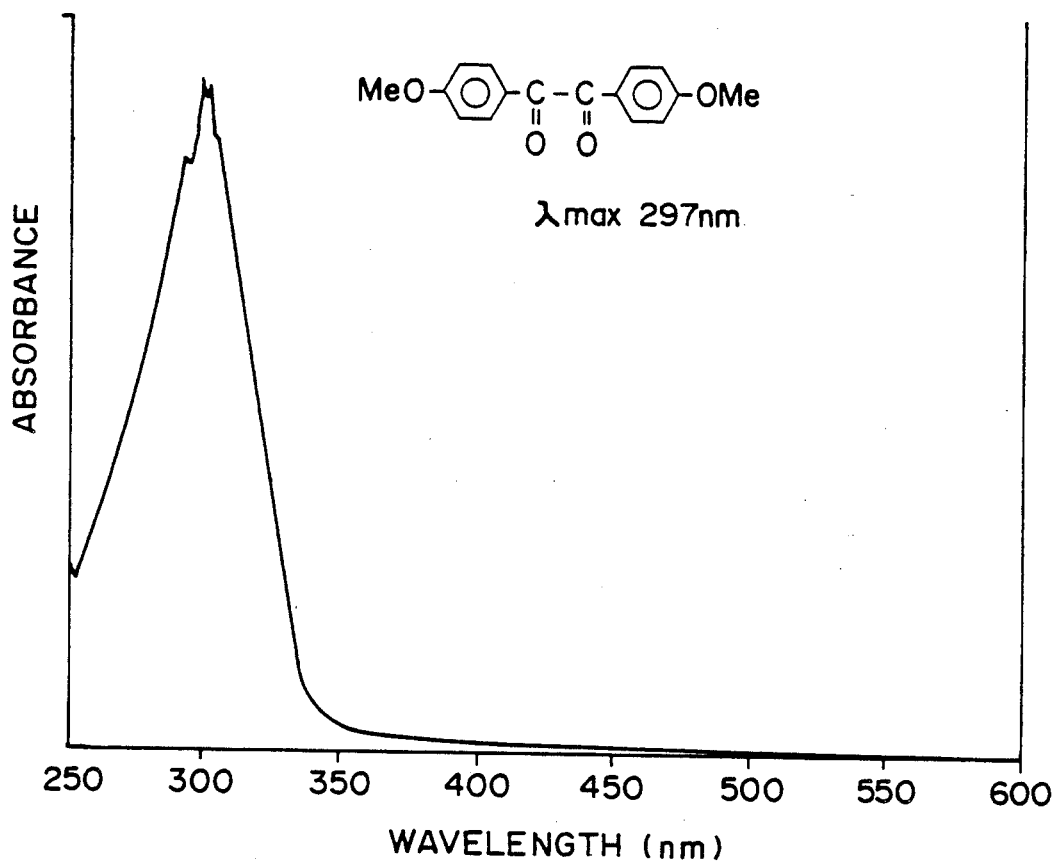
FIG. 14 through FIG. 16 are graphs showing absorption characteristics of photopolymerization initiators.
Figure 15:
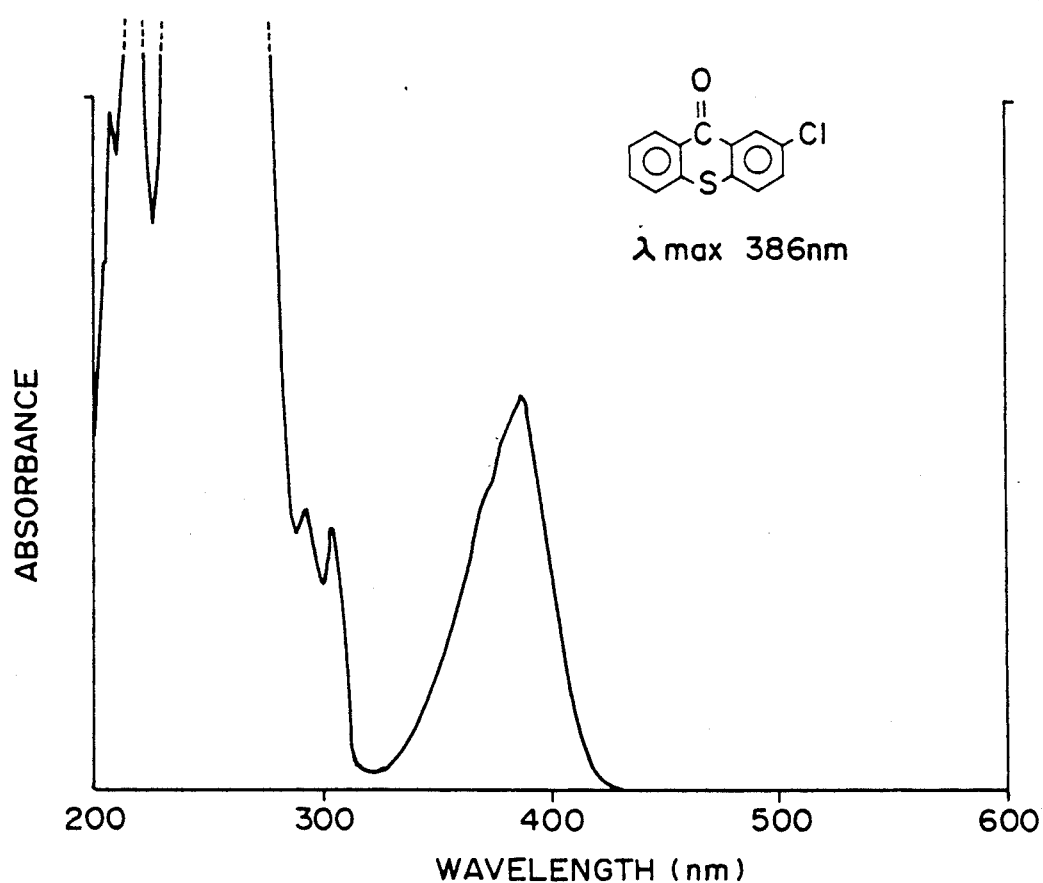
Figure 16:
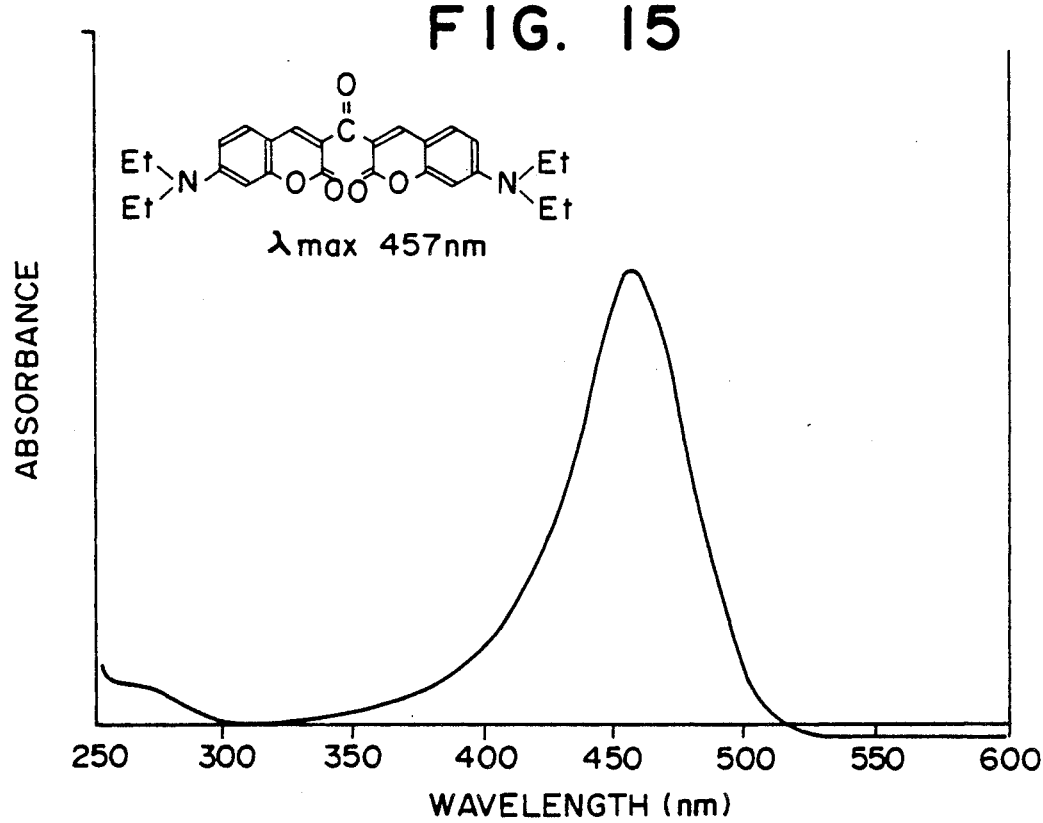

The photopolymerization initiator 4,4'-dimethoxybenzil showed the absorption characteristic shown in FIG. 14, the photopolymerization initiator 2-chlorothioxanthone the absorption characteristic shown in FIG. 15 and the photopolymerization initiator shown in Table 3 the absorption characteristic shown in FIG. 16, respectively. Here, the elements (A), (B) and (C) became magenta, cyan and yellow, respectively, during image formation.

Next, the above recording medium 1 was wound in a roll and assembled in the device shown in FIG. 3. As the thermal head 3a, a line type of A-4 size with a width of 0.2 mm and 8 dots/mm having an array of heat-generating elements 3b arranged at the edge portion was used and disposed so that the substrate 1b side of the transfer recording medium contacted the heat-generating elements 3b, so as to be pressed against the heat-generating elements 3a through the tension of the heat transfer recording medium. In this Example, as the light irradiating means, without using a combination of the rotatory member 3c and the light source 3g, three fluorescent lamps with different peak wavelengths from each other were employed (lamp A with peak wavelength 335 nm (FL10A70E35/33T15, produced by Toshiba), lamp B with peak wavelength 390 nm (F10A7-0E39/33T15, produced by Toshiba) and lamp C with peak wavelength 450 nm (FL10A70/33T15, produced by Toshiba)).

The transfer recording layer had a property of increasing its softening temperature to lose a transferability to the record paper when it was provided with light rays of a prescribed wavelength range and heat. For this reason, as shown in the timing chart of FIG. 7, for the purpose of magenta color recording, a current was supplied for 25 msec not to heating elements corresponding to an image signal of "magenta" but to heating elements corresponding to an image signal of "white" (the color of the record paper), and the fluorescent lamp A was turned on for 30 msec to effect uniform illumination.

Next, for cyan color recording, from a point of time 20 msec after the termination of the above illumination, i.e., from the point 50 msec after the commencement of the energization of the heating elements, a current was supplied for 20 msec not to heating elements corresponding to an image signal of cyan but to heating elements corresponding to an image signal of "white", and the fluorescent lamp B was turned on for 25 msec to effect uniform illumination.

Further, from a time 25 msec after the termination of the illumination from the lamp B, i.e., from a time 50 msec after the commencement of the energization for cyan color recording, a current was supplied for 15 msec not to heating elements corresponding to an image signal of "yellow" but to heating elements corresponding to an image signal of "white", and the fluorescent lamp C was turned on for 20 msec to effect uniform illumination.

In the above described manner, the thermal head was energized under control based on image signals of magenta, cyan, yellow and white to form a negative image in the transfer recording layer, while the transfer recording medium 1 was conveyed in synchronism with the operation in a repetition cycle of 150 msec/line. After the above-mentioned image was formed in this way, a plain paper with a surface smoothness of 10-30 sec was superposed onto the image bearing face of the transfer medium, and after heating under pressure, the transfer medium was separated to leave a transferred image of two colors of yellow and red on the recording paper. Thus, a multi-color of a high quality was obtained in one shot.

Separately, by forming an image of only magenta color, an image of only cyan color and an image of only yellow color were formed respectively with solid printing by use of the above recording medium, and the optical density of each color was measured by RD-514 optical densitometer of Macbeth Co. As the result, the magenta image was 1.05, the cyan image 1.10 and the yellow image 1.10, with a maximum value of fog (white portion) being 0.02 for magenta, 0.03 for cyan and 0.02 for yellow.

EXAMPLES 2-5

Recording media were prepared in the same manner as in Example 1 by changing the photopolymerization initiators in the elements (A) (B) and (C) shown in Table 1-Table 3 in Example 1 to those shown below together with amines. These recording media were evaluated similarly as in Example 1. The results are also shown below with respect solid color densities.

EXAMPLE 2

Element (A)

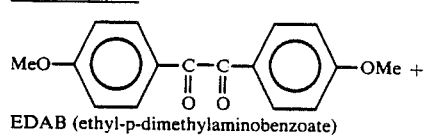

EDAB (ethyl-p-dimethylaminobenzoate)

Element (B)

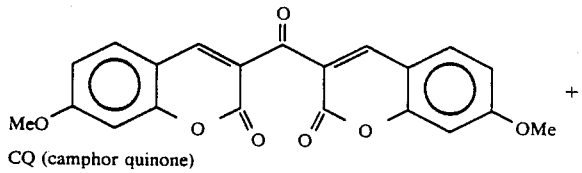

CQ (camphor quinone)

Element (C)

-continued

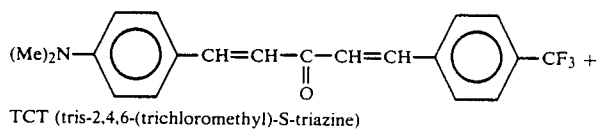

TCT (tris-2,4,6-(trichloromethyl)-S-triazine)

| Optical density at image portion | | |
|---|---|---|
| M(magenta) | C(cyan) | Y(yellow) |
| 1.10 | 1.15 | 1.20 |

EXAMPLE 3

Element (A)

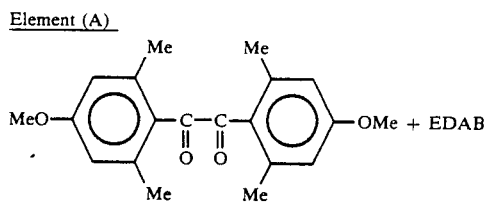

Element (B)

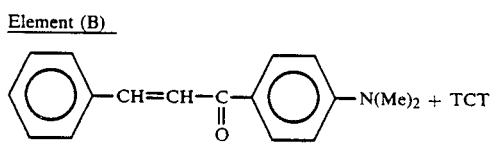

Element (C)

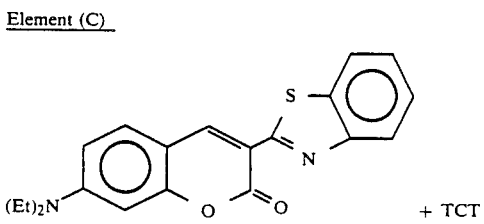

| Optical density | | |
|---|---|---|
| M | C | Y |
| 1.15 | 1.00 | 1.15 |

EXAMPLE 4

Element (A)

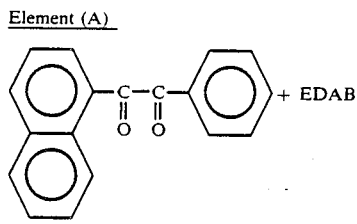

Element (B)

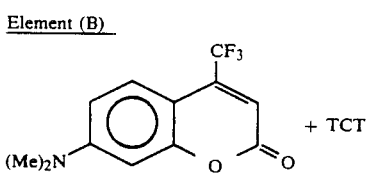

Element (C)

-continued

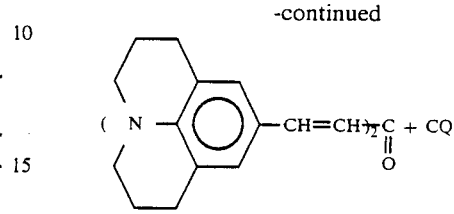

| Optical density | | |
|---|---|---|
| M | C | Y |
| 1.00 | 1.00 | 1.05 |

EXAMPLE 5

Element (A)

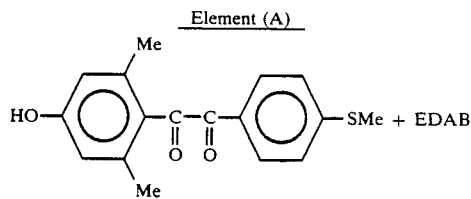

Element (B)

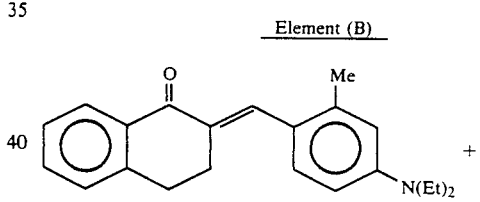

2,2',4,4',5,5'-hexaacryl-biimidazole

Element (C)

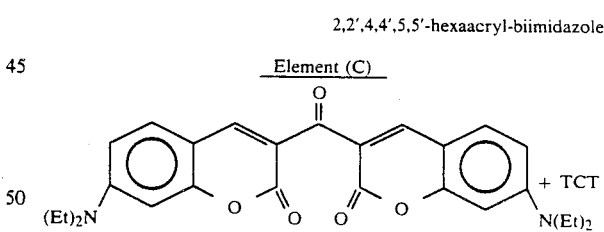

As can be understood from the above results, by use of the recording medium of the present invention, a multi-color image of high quality with little overlapping of the photosensitive wavelength regions of the photopolymerization initiators and therefore with high image density and little fog of each color can be formed.

EXAMPLE 6

TABLE 4

| Category | Components | wt. % |
|---|---|---|
| Polymerizable component | Reaction product of p-cyclohexyl-diisocyanate and hydroxypropyl acrylate | 60 |
| Binder | Chlorinated polyethylene | 23 |
| Photopolymerization initiator | 4,4'-Dimethoxybenzil | 5.5 |

TABLE 4-continued

| Category | Components | wt. % |
|---|---|---|
| Amine | Ethyl-p-dimethylaminobenzoate | 1.5 |
| Colorant | Brilliant Carmine 6B-NS (produced by Toyo Ink K.K.) | 10 |

TABLE 5

| Category | Components | wt. % |
|---|---|---|
| Polymerizable component | Reaction product of p-cyclo-hexyldiisocyanate and hydroxypropyl acrylate | 62 |
| Binder | Chlorinated polyethylene | 25 |
| Photopolymerization initiator | 2-Chlorothioxanthone | 1.5 |
| Amine | Phenyl-p-diethylaminobenzoate | 1.5 |
| Colorant | Cyanine Blue RNF (produced by Toyo Ink K.K.) | 10 |

TABLE 6

| Category | Components | wt. % |
|---|---|---|
| Polymerizable component | Reaction product of p-cyclo-hexyldiisocyanate and hydroxypropyl acrylate | 62 |
| Binder | Chlorinated polyethylene | 25 |
| Photopolymerization initiator | 3,3'-Carbonylbis(7-diethyl-amino-coumarine, | 1.5 |
| | Tris-2,4,6-(trichloromethyl)-S-triazine | 1.5 |
| Colorant | Lionol Yellow SS-OW (produced by Toyo Ink K.K.) | 10 |

With the use of the components shown in Table 4—Table 6, in the same manner as in Example 1, respective microcapsulate image-forming elements (A), (B) and (C) were prepared. The image-forming elements (A), (B) and (C) all had particle sizes of 7 to 15 μm, with an average particle size of about 10 μm.

Next, on a PET film with a thickness of 6 μm coated with a toluene solution of a polyester type adhesive 1g (Polyester LP-220), sufficiently mixed image-forming elements (A), (B) and (C) were sprayed in excessive amount. The thickness of the adhesive 1 g was made so that it became about 1 μm after drying. By blowing air gun against the image-forming elements (A), (B) and (C) on the PET film to remove the image-forming elements not in contact with the adhesive 1 g, and further the above PET film was passed through two rollers (surface temperature: 110° C.) under a pressure of 1 kg/cm² to prepare a recording medium of the present invention.

The thus prepared recording medium of the present invention was assembled in the device shown in FIG. 3, and evaluated similarly as in Example 1. However, as the light irradiating means, a combination comprising a rotatory member 3c and a light source 3g was used. The rotatory member 3c was a cylinder made of a glass with a thickness of 2 mm (trade name: DURAN 50, produced by SCHOTT Co., West Germany). Also, as the three kinds of the phosphors coated on the inner surfaces of the rotatory member 3c, thallium-activated calcium phosphate, europium-activated strontium magnesium pyrophosphate and europium-activated barium magnesium aluminate were employed.

The recorded image obtained was a multi-color image of high quality with good fixability. Also, the optical densities of the image of only magenta color, the image of only cyan color and the image of only yellow color formed by solid printing were found to be 1.25 for magenta image, 1.30 for cyan image and 1.30 for yellow image, with the maximum value of fog (white portion) being 0.02 for magenta, 0.03 for cyan and 0.02 for yellow.

EXAMPLES 7–13

Recording media were prepared in the same manner as in Example 6 by changing the photopolymerization initiators in the elements (A) (B) and (C) shown in Table 4–Table 6 in Example 6 to the combinations shown below. These recording media were evaluated similarly as in Example 6. The results are inclusively shown in Table 7 appearing hereinafter. In forming recorded images in these Examples, irradiation time of light and application time of heat were variously changed. The irradiation time of light and the application time of heat are represented by x, y, z, x', y', z' as shown in the timing chart in FIG. 17, and indicated as the image forming conditions also in Table 7 below.

EXAMPLE 7

Element (A)

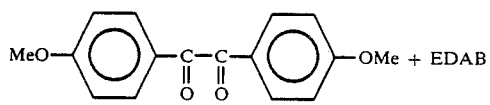

(298)

The numerical value in the parentheses following the initiator is the absorption maximum value (nm) when the initiator was measured in chloroform. (The same as hereinbelow). The abbreviation EDAB and others appearing hereinbelow are the same as used in Examples 2–5.

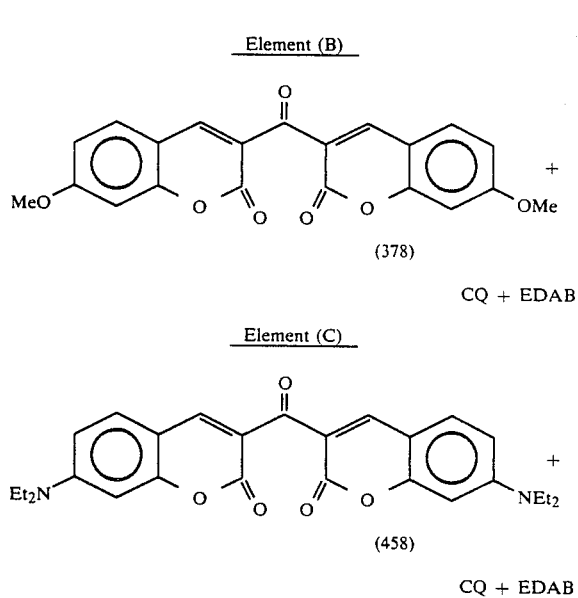

EXAMPLE 8

Element (A)

-continued

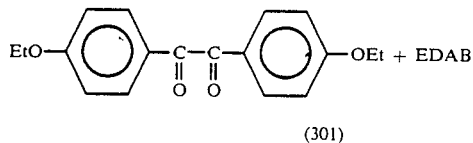
(301)

Element (B)

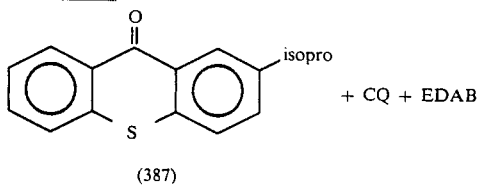
(387) + CQ + EDAB

Element (C)

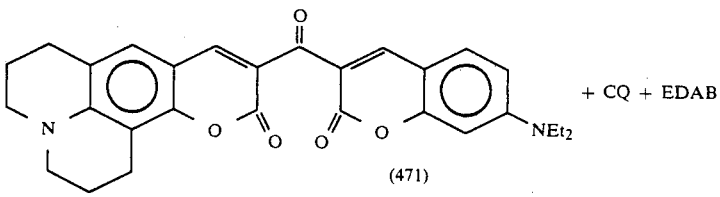
(471) + CQ + EDAB

EXAMPLE 9

Element (A)

$\begin{pmatrix} 262 \\ 278 \\ 321 \end{pmatrix}$ + EDAB

Element (B)

[structure with CF3, Et2N, coumarin] (392) + CQ + EDAB

Element (C)

[Me2N—C6H4—C=C(O)—C6H4—NMe2] (445)

CQ + EDAB

EXAMPLE 10

Element (A)

[methylenedioxyphenyl diketone structure] $\begin{pmatrix} 280 \\ 327 \end{pmatrix}$ + EDAB Element (B)

[MeO-coumarin-CO-CO-coumarin-OMe structure] (393) + TCT

Element (C)

[Et2N-coumarin-CO-CO-coumarin-NEt2 structure] + TCT

EXAMPLE 11

Element (A)

HO—C6H4—CO—CO—C6H4—OH + EDAB
(298)

Element (B)

(389) + EDAB

Element (C)

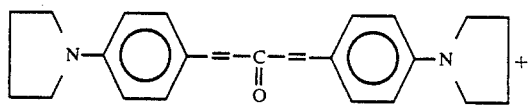

(445)

EXAMPLE 12

Element (A)

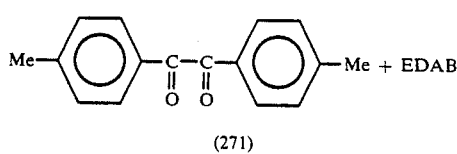

(271)

Element (B)

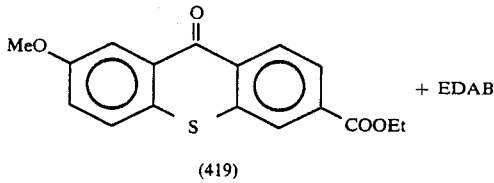

(419)

Element (C)

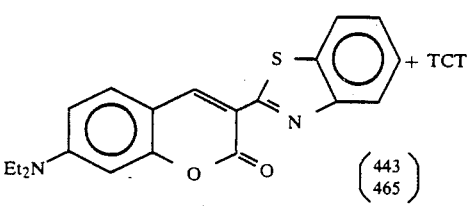

$\begin{pmatrix} 443 \\ 465 \end{pmatrix}$

EXAMPLE 13

Element (A)

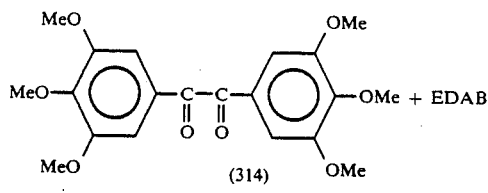

(314)

Element (B)

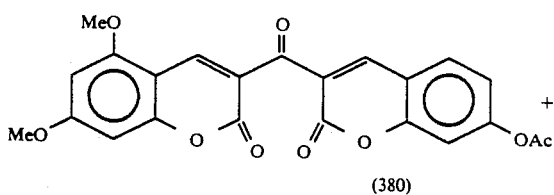

(380)

CQ + EDAB

Element (C)

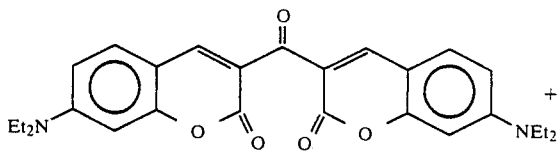

CQ + EDAB

TABLE 7

| Example | Image forming condition (ms) | | | | | | | Optical density at image portion | | |
|---|---|---|---|---|---|---|---|---|---|---|
| | x | x' | y | y' | z | z' | p | M | C | Y |
| 7 | 30 | 25 | 15 | 12 | 15 | 12 | 50 | 1.25 | 1.30 | 1.25 |
| 8 | 25 | 20 | 25 | 20 | 20 | 15 | 50 | 1.30 | 1.25 | 1.20 |
| 9 | 45 | 40 | 45 | 40 | 35 | 30 | 75 | 1.20 | 1.15 | 1.20 |
| 10 | 35 | 35 | 20 | 20 | 20 | 15 | 50 | 1.30 | 1.25 | 1.25 |
| 11 | 70 | 65 | 25 | 20 | 50 | 45 | 100 | 1.20 | 1.15 | 1.15 |
| 12 | 75 | 65 | 25 | 20 | 70 | 50 | 100 | 1.20 | 1.10 | 1.05 |
| 13 | 50 | 40 | 20 | 20 | 15 | 12 | 50 | 1.25 | 1.20 | 1.30 |

As can be understood from Table 7, by use of the recording medium of the present invention, a multicolor image of high quality with little overlapping of the photosensitive wavelength regions of the photopolymerization initiators and therefore with high image density and little fog of each color can be formed.

EXAMPLES 14–28

For further understanding of the present invention, the following experiments were conducted.

First, recording media of the present invention were prepared in the same manner as in Example 6 by changing the photopolymerization initiators in Table 4 to the photopolymerization initiators represented by the formula (I) as described above shown in Table 8 below.

Subsequently, with the recording medium placed on a hot plate with the PET film as the lower side, while heating the medium to 100° C., the photoirradiation was effected by use of the lamp A (peak wavelength 335 nm) from the transfer layer side. Next, the above recording medium was superposed on a plain paper and passed between the transfer roller 4a and the pressure roller 4c in the device shown in FIG. 3 to have the transfer layer transferred on to the plain paper. The image density of the thus obtained transferred image was measured to determine the shortest photoirradiation time when it became 0.07. For measurement of image density, RD-514 optical densitometer produced by Macbeth Co. was used. Next, similar experiments were conducted by changing the lamp A to the lamp B (peak wavelength 390 nm) and to the lamp C (peak wavelength 450 nm). The experimental results are shown in Table 8.

TABLE 8

| Example | Photopolymerization initiator | Shortest photoirradiation time in | | |
|---|---|---|---|---|
| | | lamp A | lamp B | lamp C |
| 14 | 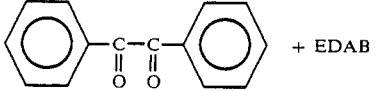 (261) + EDAB | 80 msec | 1 sec< | 1 sec< |
| 15 | 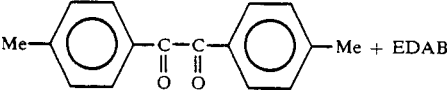 (271) Me—⟨⟩—CO—CO—⟨⟩—Me + EDAB | 50 msec | 500 ms< | 500 msec< |
| 16 | 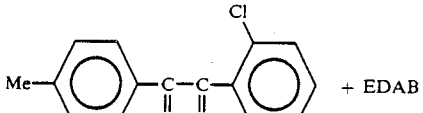 (268) Me—⟨⟩—CO—CO—⟨⟩—Cl + EDAB | 60 msec | 500 ms< | 500 msec< |
| 17 | 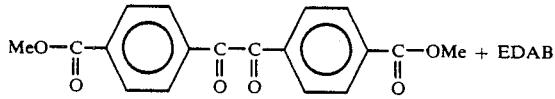 (271) MeO—CO—⟨⟩—CO—CO—⟨⟩—CO—OMe + EDAB | 100 msec | 1 sec< | 1 sec< |
| 18 | 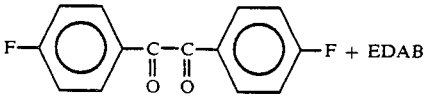 (263) F—⟨⟩—CO—CO—⟨⟩—F + EDAB | 100 msec | 1 sec< | 1 sec< |
| 19 | 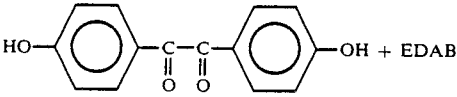 (298) HO—⟨⟩—CO—CO—⟨⟩—OH + EDAB | 50 msec | 400 msec< | 400 msec< |
| 20 | 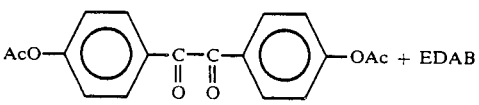 (269) AcO—⟨⟩—CO—CO—⟨⟩—OAc + EDAB | 55 msec | 400 msec< | 400 msec< |
| 21 | 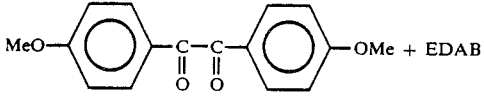 (298) MeO—⟨⟩—CO—CO—⟨⟩—OMe + EDAB | 18 msec | 100 msec | 100 msec< |
| 22 | 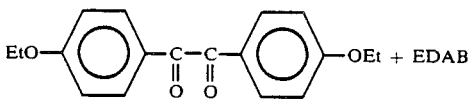 (301) EtO—⟨⟩—CO—CO—⟨⟩—OEt + EDAB | 15 msec | 100 msec | 100 msec< |

TABLE 8-continued

| Example | Photopolymerization initiator | Shortest photoirradiation time in | | |
|---|---|---|---|---|
| | | lamp A | lamp B | lamp C |
| 23 | 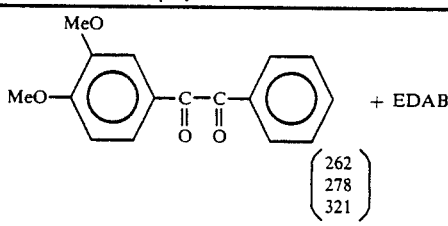 (262, 278, 321) | 27 msec | 150 msec | 200 msec< |
| 24 | 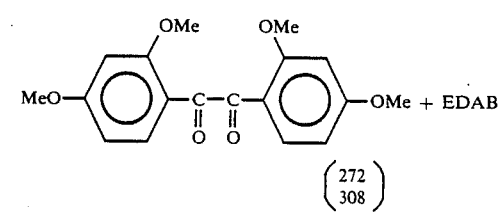 (272, 308) | 80 msec | 500 msec< | 500 msec< |
| 25 | 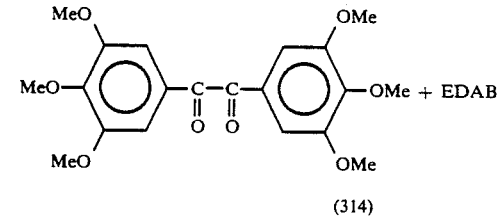 (314) | 32 msec | 150 msec | 200 msec< |
| 26 | 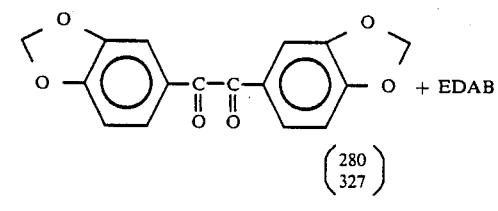 (280, 327) | 22 msec | 120 msec | 200 msec< |
| 27 | 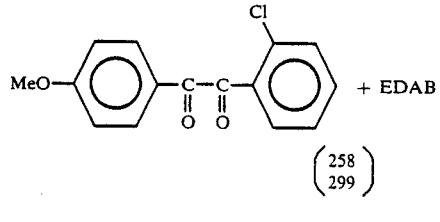 (258, 299) | 20 msec | 150 msec | 150 msec< |
| 28 | 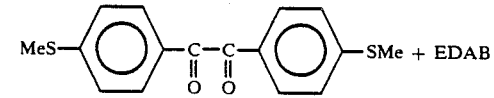 (331) | 17 msec | 100 msec | 200 msec |

As can be understood from the above Table 8, while the photopolymerization initiator represented by the formula (I) has no sensitivity to the lamp B and the lamp C, it is highly sensitive to the lamp A, and it can be appreciated that recorded image with little cross-talk can be obtained according to the recording medium of the present invention.

What is claimed is:

1. A recording medium having a recording layer comprising microcapsule image-forming elements (A), (B) and (C) containing at least a compound having unsaturated double bond and a photopolymerization initiator, said photopolymerization initiator in said microcapsule element (A) having an absorption maximum from 263 nm to 331 nm and being a compound represented by the following formula (I)

(I)

wherein $R_1$ and $R_2$ are each hydrogen atom, halogen atom, alkyl, alkoxy or alkylthio with the provision that at least one of $R_1$ and $R_2$ is not hydrogen, said photopolymerization initiator in said microcapsule element (B) having an absorption maximum in a wavelength region of 360 to 430 nm, and said photopolymerization initiator in said microcapsule element (C) having an absorption maximum in a wavelength region above 430 nm and not longer than 700 nm.

2. A recording medium according to claim 1, wherein at least one of $R_1$ and $R_2$ in said formula (I) is an alkoxy group.

3. A recording medium according to claim 1, wherein at least one of $R_1$ and $R_2$ in said formula (I) is analkylthio group.

4. A recording medium according to claim 1, wherein the photopolymerization initiator in said microcapsule (B) is thioxanthone derivative having an absorption maximum in a wavelength region of 360 to 430 nm.

5. A recording medium according to claim 1, wherein the photopolymerization initiator in said microcapsule (B) comprises a complex system containing coumarin derivative having an absorption maximum in a wavelength region of 360 to 430 nm.

6. A recording medium according to claim 5, wherein said photopolymerization initiator comprises said coumarin derivative, and either S-triazine derivative having at least one trihalomethyl group or camphor quinone.

7. A recording medium according to claim 1, wherein the photopolymerization initiator in said microcapsule (C) comprises a compound having an absorption maximum in a wavelength region of above 430 nm and not longer than 700 nm represented by the formula shown below, and either S-triazine derivative having at least one trihalomethyl group or camphor quinone:

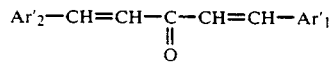

wherein $Ar'_1$ and $Ar'_2$ are each aromatic ring or heterocyclic ring, and at least one of the $Ar'_1$ and $Ar'_2$ has a nitrogen-containing group.

8. A recording medium according to claim 1, wherein the photopolymerization initiator in said microcapsule (C) comprises a complex system containing coumarin derivative having an absorption maximum in a wavelength region of above 430 nm and not longer than 700 nm.

9. A recording medium according to claim 8, wherein said photopolymerization initiator comprises said coumarin derivative, and either S-triazine derivative having at least one trihalomethyl group or camphor quinone.

10. A recording medium according to claim 1, wherein said microcapsules (A), (B) and (C) change their transfer characteristics when provided with the light having peak wavelengths in said wavelength regions and heat.

* * * * *

UNITED STATES PATENT AND TRADEMARK OFFICE
CERTIFICATE OF CORRECTION

PATENT NO. : 4,992,351
DATED : February 12, 1991
INVENTOR(S) : NORIO OHKUMA, ET AL.

Page 1 of 5

It is certified that error appears in the above-identified patent and that said Letters Patent is hereby corrected as shown below:

IN [57] ABSTRACT

Line 8, "cyclis" should read --cyclic--.

SHEET 7 OF 15

FIG. 7, "MEATING" should read --HEATING--.

SHEET 15 OF 15

Figure 17:
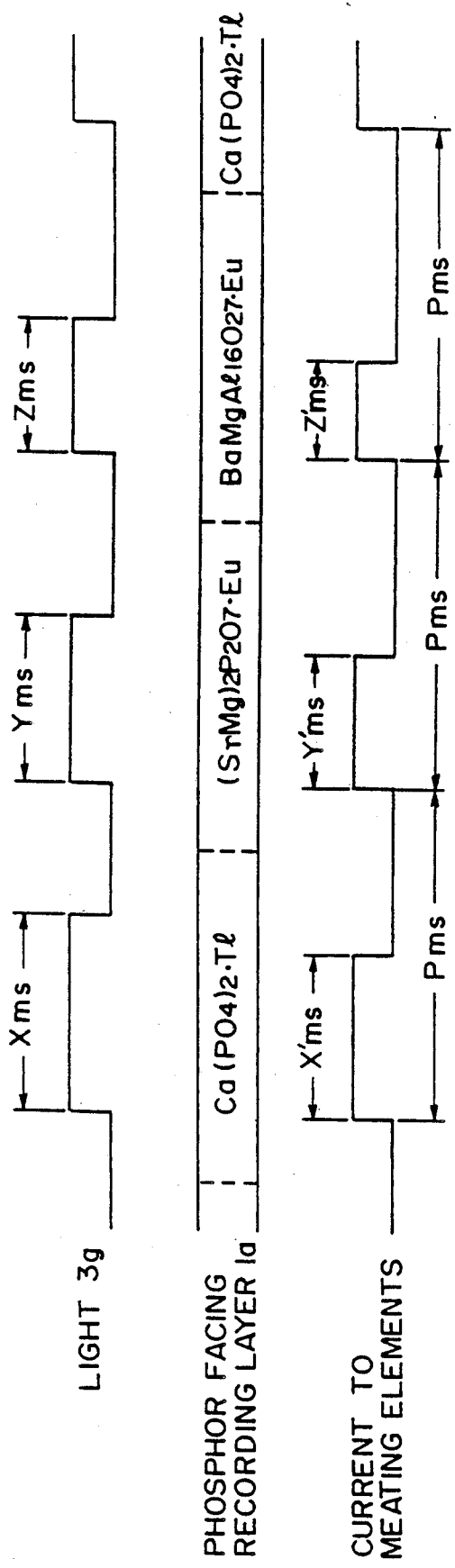

FIG. 17, "MEATING" should read --HEATING--.

COLUMN 1

Line 65, "CAr$_1$" should read --C—Ar$_1$--.

COLUMN 2

Line 27, "thalliumactivated" should read --thallium-activated--.
Line 30, "430 mn," should read --430 nm,--.

COLUMN 3

Line 11, "less, the" should read --less.  They--.

COLUMN 4

Line 24, "ethilthio," should read --ethylthio,--.
Line 36, "contained. Specific" should read --contained. ¶ Specific--.

UNITED STATES PATENT AND TRADEMARK OFFICE
CERTIFICATE OF CORRECTION

PATENT NO. : 4,992,351

DATED : February 12, 1991

INVENTOR(S) : NORIO OHKUMA, ET AL.

It is certified that error appears in the above-identified patent and that said Letters Patent is hereby corrected as shown below:

COLUMN 9

Line 67, Insert -- Synthesis Example 4,4'-dimethoxybenzil:--.

COLUMN 11

Line 52, "m.P 113-115°C." should read --m.p. 113-115°C.--.

COLUMN 12

Line 39, "antone" should read --anthone--.
    Line 49, "coumaine" should read --coumarin--.

COLUMN 13

Line 22, "amines  The" should read --amines.  The--.

COLUMN 17

Line 45, "skeletone" should read --skeleton--.

COLUMN 18

Line 8, "composition" should read --composition.--.
    Line 18, "etc  Also," should read --etc.  Also,--.
    Line 68, "phaseseparation" should read --phase separaton--.

UNITED STATES PATENT AND TRADEMARK OFFICE
CERTIFICATE OF CORRECTION

PATENT NO. : 4,992,351
DATED : February 12, 1991
INVENTOR(S) : NORIO OHKUMA, ET AL.

Page 3 of 5

It is certified that error appears in the above-identified patent and that said Letters Patent is hereby corrected as shown below:

COLUMN 19

Line 5, "etc" should read --etc.--.
    Line 10, "imageforming" should read --image-forming--.
    Line 27, "transferreceiving" should read
        --transfer-receiving--.
    Line 39, "abovementioned" should read
        --above-mentioned--.

COLUMN 20

Line 47, "higher" should read --higher.--.
    Line 58, "seconds The" should read --seconds. The--.

COLUMN 21

Line 4, "ature At" should read --ature. At--.
    Line 21, "obtain a recorded" should read
        --obtains a recording--.
    Line 28, "at least" should read --at at least--.
    Line 47, "changed Herein," should read --changed.
        Herein--.

COLUMN 22

Figure 2C:
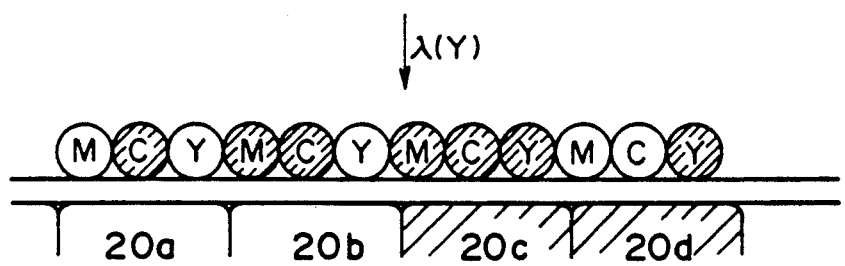
Figure 2D:
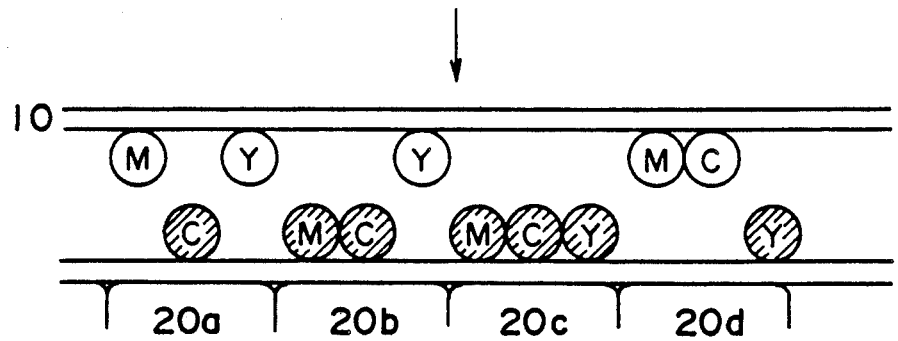

Line 50, "FIG. 3C," should read --FIG. 2C,--.

COLUMN 23

Line 43, "4with" should read --4a with--.

UNITED STATES PATENT AND TRADEMARK OFFICE
CERTIFICATE OF CORRECTION

PATENT NO. : 4,992,351
DATED : February 12, 1991
INVENTOR(S) : NORIO OHKUMA, ET AL.

It is certified that error appears in the above-identified patent and that said Letters Patent is hereby corrected as shown below:

COLUMN 24

Line 40, "the only" should read --only the--.

COLUMN 25

Line 45, "innerside" should read --inside--.
Line 54, "FIG. 6A The" should read --FIG. 6A. The--.

COLUMN 26

Line 7, "herein-after" should read --hereinafter--.
Line 58, "transfer recording 1a" should read --transfer recording layer 1a--.
Line 64, "heatgenerating" should read --heat-generating--.

COLUMN 27

Line 58, "or" should read --of--.
Line 66, "Examples Here," should read --Examples. Here,--.

COLUMN 34

Line 12, "elements (A)(B)" should read --elements (A), (B)--.

COLUMN 42

Line 55, "formula (I)" should read --formula (I):--.

UNITED STATES PATENT AND TRADEMARK OFFICE
CERTIFICATE OF CORRECTION

PATENT NO. : 4,992,351
DATED : February 12, 1991
INVENTOR(S) : NORIO OHKUMA, ET AL.

It is certified that error appears in the above-identified patent and that said Letters Patent is hereby corrected as shown below:

COLUMN 43

Line 8, "anal-" should read --an al- --.

Signed and Sealed this

Seventeenth Day of November, 1992

Attest:

DOUGLAS B. COMER

*Attesting Officer*     *Acting Commissioner of Patents and Trademarks*